US010626073B2

(12) United States Patent
Farmer et al.

(10) Patent No.: US 10,626,073 B2
(45) Date of Patent: Apr. 21, 2020

(54) PROCESS FOR PRODUCTION OF ACRYLIC ACID

(71) Applicant: Novomer, Inc., Boston, MA (US)

(72) Inventors: Jay J. Farmer, Boston, MA (US); Peter Galebach, Madison, WI (US); Kyle Sherry, Rochester, NY (US); Sadesh H. Sookraj, Cambridge, MA (US)

(73) Assignee: Novomer, Inc., Rochester, NY (US)

(*) Notice: Subject to any disclaimer, the term of this patent is extended or adjusted under 35 U.S.C. 154(b) by 0 days.

(21) Appl. No.: 16/107,858

(22) Filed: Aug. 21, 2018

(65) Prior Publication Data

US 2018/0354881 A1    Dec. 13, 2018

Related U.S. Application Data

(62) Division of application No. 15/550,193, filed as application No. PCT/US2016/017868 on Feb. 12, 2016, now Pat. No. 10,099,988.

(60) Provisional application No. 62/116,325, filed on Feb. 13, 2015.

(51) Int. Cl.
*C07C 51/09* (2006.01)
*C07C 57/04* (2006.01)

(52) U.S. Cl.
CPC .............. *C07C 51/09* (2013.01); *C07C 57/04* (2013.01); *Y02P 20/125* (2015.11)

(58) Field of Classification Search
CPC ... C07C 51/00; C07C 51/09; C07C 57/00–04; Y02P 20/00; Y02P 20/10; Y02P 20/12; Y02P 20/121; Y02P 20/125
See application file for complete search history.

(56) References Cited

U.S. PATENT DOCUMENTS

| | | | |
|---|---|---|---|
| 2,245,404 A | 6/1941 | Kise et al. |
| 2,302,321 A | 11/1942 | Hopff et al. |
| 2,361,036 A | 10/1944 | Kung |
| 2,375,005 A | 5/1945 | Kung |
| 2,469,704 A | 5/1949 | Stone |
| 2,525,794 A | 10/1950 | Gresham et al. |
| 2,526,554 A | 10/1950 | Gresham et al. |
| 2,691,643 A | 10/1954 | Chirtel et al. |
| 3,002,017 A | 9/1961 | Wearsch et al. |
| 3,176,042 A | 3/1965 | Schnizer et al. |
| 3,211,706 A | 10/1965 | Börner |
| 3,326,938 A | 6/1967 | Wagner |
| 3,418,338 A | 12/1968 | Gilman et al. |
| 3,525,718 A | 8/1970 | Derieg et al. |
| 3,751,435 A | 8/1973 | Van Der Ven et al. |
| 3,800,006 A | 3/1974 | Katayama et al. |
| 3,954,854 A | 5/1976 | Gehrmann et al. |
| 4,026,967 A | 5/1977 | Flexman, Jr. et al. |
| 4,081,253 A | 3/1978 | Marion |
| 4,221,727 A | 9/1980 | Tsang et al. |
| 4,317,926 A | 3/1982 | Sato et al. |
| 4,590,293 A | 5/1986 | Pascoe |
| 4,792,620 A | 12/1988 | Paulik et al. |
| 4,873,378 A | 10/1989 | Murphy et al. |
| 5,096,470 A | 3/1992 | Krishnamurthy |
| 5,198,578 A | 3/1993 | Etzkorn et al. |
| 5,705,688 A | 1/1998 | Fauconet et al. |
| 5,731,252 A | 3/1998 | Warner et al. |
| 6,123,812 A | 9/2000 | Bessling et al. |
| 6,147,126 A | 11/2000 | DeGeorge et al. |
| 6,252,110 B1 | 6/2001 | Uemura et al. |
| 6,348,611 B1 | 2/2002 | Lee et al. |
| 6,392,078 B1 | 5/2002 | Ryu et al. |
| 6,492,535 B1 | 12/2002 | Castiglioni et al. |
| 6,541,665 B1 | 4/2003 | Bastiaensen et al. |
| 6,573,340 B1 | 6/2003 | Khemani et al. |
| 6,773,578 B1 | 8/2004 | O'Rear et al. |
| 6,852,865 B2 | 2/2005 | Coates et al. |
| 6,916,951 B2 | 7/2005 | Tustin et al. |
| 8,277,660 B2 | 10/2012 | Kimball et al. |
| 8,445,703 B2 | 5/2013 | Allen et al. |
| 8,796,475 B2 | 8/2014 | Allen et al. |
| 9,096,510 B2 | 8/2015 | Porcelli et al. |
| 9,115,070 B2 | 8/2015 | Pazicky et al. |
| 9,156,803 B2 | 10/2015 | Allen et al. |
| 9,206,144 B2 | 12/2015 | Allen et al. |
| 9,327,280 B2 | 5/2016 | Lee et al. |
| 9,403,788 B2 | 8/2016 | Lee et al. |
| 9,493,391 B2 | 11/2016 | Allen et al. |
| 9,738,784 B2 | 8/2017 | Allen et al. |
| 9,914,689 B2 | 3/2018 | Porcelli et al. |
| 10,065,914 B1 | 9/2018 | Ruhl et al. |
| 10,099,988 B2 | 10/2018 | Farmer et al. |

(Continued)

FOREIGN PATENT DOCUMENTS

| | | |
|---|---|---|
| CN | 103822811 A | 5/2014 |
| EP | 352850 A1 | 1/1990 |

(Continued)

OTHER PUBLICATIONS

International Search Report and Written Opinion received for PCT Patent Application No. PCT/US2018/022248, dated May 24, 2018, 10 pages.
International Search Report and Written Opinion received for PCT Patent Application No. PCT/US2017/059243, dated Feb. 1, 2018, 10 pages.
International Search Report and Written Opinion received for PCT Patent Application No. PCT/US2017/059249, dated Feb. 22, 2018, 11 pages.
International Search Report and Written Opinion received for PCT Patent Application No. PCT/US2018/014243, dated Mar. 28, 2018, 11 pages.

(Continued)

*Primary Examiner* — Natasha E Young
(74) *Attorney, Agent, or Firm* — Young Basile Hanlon & MacFarlane, P.C.

(57) ABSTRACT

Provided are integrated processes for the conversion of beta propiolactone to acrylic acid. Systems for the production of acrylic acid are also provided.

6 Claims, No Drawings

(56) References Cited

U.S. PATENT DOCUMENTS

| | | |
|---|---|---|
| 10,099,989 B2 | 10/2018 | Sookraj |
| 10,144,802 B2 | 12/2018 | Sookraj |
| 10,221,150 B2 | 3/2019 | Farmer et al. |
| 10,221,278 B2 | 3/2019 | Lee et al. |
| 10,245,559 B2 | 4/2019 | Lapointe et al. |
| 2003/0098274 A1 | 5/2003 | Lee et al. |
| 2003/0162961 A1 | 8/2003 | Coates et al. |
| 2004/0102532 A1 | 5/2004 | Landis et al. |
| 2005/0014977 A1 | 1/2005 | Drent et al. |
| 2005/0196343 A1 | 9/2005 | Reddy et al. |
| 2005/0209411 A1 | 9/2005 | Nestler et al. |
| 2005/0222458 A1 | 10/2005 | Craciun et al. |
| 2005/0240032 A1 | 10/2005 | Luinstra et al. |
| 2006/0189833 A1 | 8/2006 | Powell et al. |
| 2007/0155984 A1 | 7/2007 | Sielcken et al. |
| 2007/0217965 A1 | 9/2007 | Johnson et al. |
| 2007/0225522 A1 | 9/2007 | Kobayashi et al. |
| 2007/0293695 A1 | 12/2007 | Zoeller et al. |
| 2009/0075295 A1 | 3/2009 | Lindsey |
| 2009/0124787 A1 | 5/2009 | Preishuber-Pflugl et al. |
| 2009/0173694 A1 | 7/2009 | Peinemann et al. |
| 2009/0178495 A1 | 7/2009 | Steigmiller et al. |
| 2009/0253934 A1 | 10/2009 | Ho et al. |
| 2009/0287000 A1 | 11/2009 | Coates et al. |
| 2009/0287280 A1 | 11/2009 | Wong et al. |
| 2009/0299032 A1 | 12/2009 | Allen |
| 2010/0323573 A1 | 12/2010 | Chu et al. |
| 2010/0323885 A1 | 12/2010 | Herfert et al. |
| 2011/0065894 A1 | 3/2011 | Allen |
| 2011/0226697 A1 | 9/2011 | McLellan et al. |
| 2011/0301027 A1 | 12/2011 | Bitis et al. |
| 2011/0319849 A1 | 12/2011 | Collias et al. |
| 2012/0108695 A1 | 5/2012 | Won et al. |
| 2012/0123137 A1 | 5/2012 | Allen et al. |
| 2012/0189861 A1 | 7/2012 | Matsumoto et al. |
| 2012/0202951 A1 | 8/2012 | Gartner et al. |
| 2013/0004454 A1 | 1/2013 | Weiss et al. |
| 2013/0072645 A1 | 3/2013 | Balduf et al. |
| 2013/0165670 A1 | 6/2013 | Allen et al. |
| 2013/0209775 A1 | 8/2013 | Allen et al. |
| 2013/0274697 A1 | 10/2013 | Godlewski et al. |
| 2013/0281715 A1 | 10/2013 | Allen et al. |
| 2013/0299417 A1 | 11/2013 | Luchinger et al. |
| 2014/0018570 A1 | 1/2014 | Pazicky et al. |
| 2014/0018574 A1 | 1/2014 | Raith et al. |
| 2014/0221702 A1 | 8/2014 | Weston et al. |
| 2014/0275575 A1 | 9/2014 | Allen et al. |
| 2014/0296522 A1 | 10/2014 | Lee et al. |
| 2014/0309399 A1 | 10/2014 | Porcelli et al. |
| 2015/0005513 A1 | 1/2015 | Lee et al. |
| 2015/0141693 A1 | 5/2015 | Allen et al. |
| 2015/0183708 A1 | 7/2015 | Harris et al. |
| 2015/0299083 A1 | 10/2015 | Porcelli et al. |
| 2015/0368394 A1 | 12/2015 | Allen |
| 2016/0016876 A1 | 1/2016 | Mahoney |
| 2016/0102040 A1 | 4/2016 | Allen et al. |
| 2016/0102068 A1 | 4/2016 | Allen et al. |
| 2016/0204465 A1 | 7/2016 | Mimura et al. |
| 2016/0288057 A1 | 10/2016 | Lapointe et al. |
| 2017/0029352 A1 | 2/2017 | Sookraj et al. |
| 2017/0073463 A1 | 3/2017 | Lee et al. |
| 2017/0080409 A1 | 3/2017 | Farmer et al. |
| 2017/0096407 A1 | 4/2017 | Sookraj |
| 2017/0107103 A1 | 4/2017 | Sookraj et al. |
| 2017/0145126 A1 | 5/2017 | Mahoney |
| 2017/0225157 A1 | 8/2017 | Lee |
| 2017/0247309 A1 | 8/2017 | Porcelli et al. |
| 2017/0267618 A1 | 9/2017 | Sookraj et al. |
| 2018/0016219 A1 | 1/2018 | Farmer et al. |
| 2018/0022677 A1 | 1/2018 | Sookraj |
| 2018/0029005 A1 | 2/2018 | Sookraj |
| 2018/0030014 A1 | 2/2018 | Sookraj et al. |
| 2018/0030015 A1 | 2/2018 | Farmer et al. |
| 2018/0030201 A1 | 2/2018 | Farmer et al. |
| 2018/0057619 A1 | 3/2018 | Sookraj |
| 2018/0094100 A1 | 4/2018 | Farmer et al. |
| 2018/0153746 A1 | 6/2018 | Sookraj |
| 2018/0155491 A1 | 6/2018 | Sookraj |
| 2018/0282251 A1 | 10/2018 | Sookraj |
| 2018/0305286 A1 | 10/2018 | Sookraj |
| 2018/0305289 A1 | 10/2018 | Sookraj et al. |
| 2018/0354882 A1 | 12/2018 | Sookraj |
| 2019/0002385 A1 | 1/2019 | Sookraj |
| 2019/0030520 A1 | 1/2019 | Lee |
| 2019/0031592 A1 | 1/2019 | Sookraj et al. |
| 2019/0047972 A1 | 2/2019 | Sookraj |
| 2019/0071538 A1 | 3/2019 | Sookraj |
| 2019/0076834 A1 | 3/2019 | Sookraj |
| 2019/0076835 A1 | 3/2019 | Sookraj |
| 2019/0106532 A1 | 4/2019 | Sookraj |

FOREIGN PATENT DOCUMENTS

| | | |
|---|---|---|
| EP | 441447 A1 | 8/1991 |
| EP | 2325214 A1 | 5/2011 |
| GB | 655387 A | 7/1951 |
| GB | 762138 A | 11/1956 |
| JP | 57-14596 A | 1/1982 |
| JP | 4356292 B2 | 11/2009 |
| WO | 2002/09781 A2 | 2/2002 |
| WO | 2006/087556 A1 | 8/2006 |
| WO | 2010/118128 A1 | 10/2010 |
| WO | 2010/137974 A1 | 12/2010 |
| WO | 2011/123558 A1 | 10/2011 |
| WO | 2011/163309 A2 | 12/2011 |
| WO | 2012/030619 A1 | 3/2012 |
| WO | 2012/051219 A2 | 4/2012 |
| WO | 2012/158573 A1 | 11/2012 |
| WO | 2013/063191 A1 | 5/2013 |
| WO | 2013/067460 A1 | 5/2013 |
| WO | 2013/068846 A1 | 5/2013 |
| WO | 2013/122905 A1 | 8/2013 |
| WO | 2013/126375 A1 | 8/2013 |
| WO | 2013/180659 A1 | 12/2013 |
| WO | 2013/185009 A1 | 12/2013 |
| WO | 2014/004858 A1 | 1/2014 |
| WO | 2014/008232 A2 | 1/2014 |
| WO | 2015/085295 A2 | 6/2015 |
| WO | 2015/110321 A1 | 7/2015 |
| WO | 2015/138975 A1 | 9/2015 |
| WO | 2015/171372 A1 | 11/2015 |
| WO | 2015/184289 A1 | 12/2015 |
| WO | 2016/015019 A1 | 12/2015 |
| WO | 2016/130947 A1 | 8/2016 |
| WO | 2016/130977 A1 | 8/2016 |
| WO | 2016/130988 A1 | 8/2016 |
| WO | 2016/130993 A1 | 8/2016 |
| WO | 2016/130998 A1 | 8/2016 |
| WO | 2016/131001 A1 | 8/2016 |
| WO | 2016/131003 A1 | 8/2016 |
| WO | 2016/131004 A1 | 8/2016 |
| WO | 2017/023777 A1 | 2/2017 |
| WO | 2017/023820 A1 | 2/2017 |
| WO | 2017/165323 A1 | 9/2017 |
| WO | 2017/165344 A1 | 9/2017 |
| WO | 2017/165345 A1 | 9/2017 |
| WO | 2018/085251 A1 | 5/2018 |
| WO | 2018/085254 A1 | 5/2018 |
| WO | 2018/106824 A1 | 6/2018 |
| WO | 2018/136638 A1 | 7/2018 |
| WO | 2018/144998 A1 | 8/2018 |
| WO | 2018/170006 A1 | 9/2018 |
| WO | 2018/200466 A1 | 11/2018 |
| WO | 2018/200471 A1 | 11/2018 |
| WO | 2019/006366 A1 | 1/2019 |
| WO | 2019/006377 A1 | 1/2019 |
| WO | 2019/050649 A1 | 3/2019 |

(56) References Cited

FOREIGN PATENT DOCUMENTS

| WO | 2019/051184 A1 | 3/2019 |
|---|---|---|
| WO | 2019/070981 A1 | 4/2019 |

OTHER PUBLICATIONS

Ganji et al., "In Situ Generation of the Coatescatalyst: a Practical and Versatile Catalytic System for the Carbonylation of Meso-Epoxides", ChemInform Abstract, vol. 42, Issue 39, 2011, 1 page.
Ganji et al., "In Situ Generation of the Coates Catalyst: A Practical and Versatile Catalytic System for the Carbonylation of Meso-Epoxides", Organic Letters, vol. 13, No. 12, 2011, pp. 3142-3145.
Getzler et al., "Synthesis of β-Lactones: A Highly Active and Selective Catalyst for Epoxide Carbonylation", Journal of the American Chemical Society. vol. 124, No. 7, 2002, pp. 1174-1175.
International Search Report and Written Opinion received for PCT Patent Application No. PCT/US2016/017875, dated May 6, 2016, 16 pages.
International Search Report and Written Opinion received for PCT Patent Application No. PCT/US2016/017844, dated May 6, 2016, 10 pages.
International Search Report and Written Opinion received for PCT Patent Application No. PCT/US13/25683, dated Apr. 23, 2013, 8 pages.
International Search Report and Written Opinion received for PCT Patent Application No. PCT/US17/23302, dated Jun. 5, 2017, 9 pages.
International Search Report and Written Opinion received for PCT Patent Application No. PCT/US17/23303, dated Jun. 7, 2017, 18 pages.
International Search Report and Written Opinion received for PCT Patent Application No. PCT/US2010/030230, dated Jun. 10, 2010, 17 pages.
International Search Report and Written Opinion received for PCT Patent Application No. PCT/US2011/049125, dated Jan. 11, 2012, 10 pages.
International Search Report and Written Opinion received for PCT Patent Application No. PCT/US2012/037675, dated Aug. 9, 2012, 12 pages.
International Search Report and Written Opinion received for PCT Patent Application No. PCT/US2012/061791, dated Feb. 8, 2013, 10 pages.
International Search Report and Written Opinion received for PCT Patent Application No. PCT/US2013/026810, dated Apr. 30, 2013, 8 pages.
International Search Report and Written Opinion received for PCT Patent Application No. PCT/US2013/048238, dated Dec. 3, 2013, 8 pages.
International Search Report and Written Opinion received for PCT Patent Application No. PCT/US2013/049026, dated Dec. 17, 2013, 9 pages.
International Search Report and Written Opinion received for PCT Patent Application No. PCT/US2014/069066, dated Mar. 16, 2015, 10 pages.
International Search Report and Written Opinion received for PCT Patent Application No. PCT/US2015/020562, dated Jun. 18, 2015, 9 pages.
International Search Report and Written Opinion received for PCT Patent Application No. PCT/US2015/028123, dated Jul. 23, 2015, 7 pages.
International Search Report and Written Opinion received for PCT Patent Application No. PCT/US2015/033232, dated Aug. 19, 2015, 8 pages.
International Search Report and Written Opinion received for PCT Patent Application No. PCT/US2015/042124, dated Dec. 15, 2015, 14 pages.
International Search Report and Written Opinion received for PCT Patent Application No. PCT/US2016/017797, dated May 5, 2016, 9 pages.
International Search Report and Written Opinion received for PCT Patent Application No. PCT/US2016/017861, dated Apr. 29, 2016, 25 pages.
International Search Report and Written Opinion received for PCT Patent Application No. PCT/US2016/017878, dated May 2, 2016, 9 pages.
International Search Report and Written Opinion received for PCT Patent Application No. PCT/US2016/017880, dated Apr. 29, 2016, 9 pages.
International Search Report and Written Opinion received for PCT Patent Application No. PCT/US2016/017881, dated May 2, 2016, 8 pages.
International Search Report and Written Opinion received for PCT Patent Application No. PCT/US2016/044772, dated Nov. 8, 2016, 17 pages.
International Search Report and Written Opinion received for PCT Patent Application No. PCT/US2016/044927, dated Nov. 8, 2016, 17 pages.
International Search Report and Written Opinion received for PCT Patent Application No. PCT/US2016/017868, dated May 2, 2016, 9 pages.
International Preliminary Report on Patentability received for PCT Patent Application No. PCT/US2016/017868, dated Aug. 24, 2017, 7 pages.
Iwabuchi et al., "The Thermal Degradation of Poly(Oxycarbonylethylene) (Poly-β-Propiolactone)", Die Makromolekulare Chemie, vol. 165, 1973, pp. 59-72.
Nørskov et al., "Towards the Computational Design of Solid Catalysts", Nature Chemistry, vol. 1, Apr. 2009, pp. 37-46.
Notice of Allowance received for U.S. Appl. No. 15/550,193 dated May 23, 2018, 13 pages.
Rowley et al., "Catalytic Double Carbonylation of Epoxides to Succinic Anhydrides: Catalyst Discovery, Reaction Scope, and Mechanism", Journal of the American Chemical Society, vol. 129, No. 16, 2007, pp. 4948-4960.
Slowik et al., "Catalytic Conversion of Waste Carbon Monoxide to Valuable Chemicals & Materials", Clean Technology, 2010, pp. 283-286.
Stanghellini et al., "Redox Reactions of Metal Carbonyls. I. Kinetics and Mechanism of Disproportionation of Co2 (Co)8 with Piperidine", Inorganica Chimica Acta, vol. 22, 1977, pp. 19-22.
Trimm, D L et al., "Minimisation of Carbon Monoxide in a Hydrogen Stream for Fuel Cell Application", Applied Catalysis A: General, vol. 296, 2005, pp. 1-11.
"Understanding Biobased Carbon Content", Society of the Plastics Industry Bioplastics Council, Feb. 2012, pp. 1-12.
Extended European Search Report (includes Supplementary European Search Report and Search Opinion) received for European Patent Application No. 16750017.2, dated Sep. 6, 2018, 8 pages.

PROCESS FOR PRODUCTION OF ACRYLIC ACID

CROSS-REFERENCE TO RELATED APPLICATIONS

This application is a Divisional of U.S. patent application Ser. No. 15/550,193, now U.S. Pat. No. 10,099,988, filed Aug. 10, 2017, which is a U.S. National Phase Patent Application of PCT/US2016/017868, now WO/2016/130993, filed Feb. 12, 2016, which claims priority to and the benefit of U.S. Provisional Patent Application No. 62/116,325, filed Feb. 13, 2015, each of which is incorporated herein by reference in its entirety.

FIELD

The present disclosure relates generally to the production of acrylic acid, and more specifically to the production of acrylic acid from beta propiolactone.

BACKGROUND

Superabsorbent polymers (SAPs) are used in a variety of industrial and consumer applications, ranging from disposable hygiene products to cable water blocking. SAPs are mostly commonly manufactured by polymerization of acrylic acid. Acrylic acid production is a large industry that uses variety of methods having a range of cost efficiencies and yielding acrylic acid of varying purity. Given the size of the acrylic acid market and the importance of downstream applications of acrylic acid, there is a need for methods for producing acrylic acid with increased efficiency.

Methods have been described where beta propiolactone (BPL) is converted to acrylic acid (AA) by heating in the presence of water or alcohols, which act as catalysts to open the BPL to hydracrylic acid (3-hydroxy propionic acid) or hydracrylic acid esters, respectively. However, these methods are ill-suited to the production of glacial acrylic acid (GAA) because the water or alcohol used to catalyze the reaction can contaminate the acrylic acid stream. Thus, alternative methods to produce acrylic acid are desired.

BRIEF SUMMARY

In some aspects, provided is a method for producing acrylic acid, comprising:
(a) providing a feedstock stream comprising beta propiolactone;
(b) directing the feedstock stream to a reaction zone where it is contacted with a suitable polymerization catalyst and where at least a portion of the beta propiolactone is converted to poly(propiolactone);
(c) maintaining the reaction zone at a temperature at or above the pyrolysis temperature of poly(propiolactone) such that the thermal decomposition of poly(propiolactone) produces acrylic acid; and
(d) withdrawing an acrylic acid product stream from the reaction zone;
wherein steps (b) and (c) occur in the same reaction zone.

In other aspects, provided is a method for producing acrylic acid, comprising:
(a) providing a feedstock stream comprising beta propiolactone;
(b) directing the feedstock stream to a first reaction zone, wherein the feedstock stream is contacted with a polymerization catalyst and wherein at least a portion of the beta propiolactone is converted to a poly(propiolactone) product stream, wherein the first reaction zone is maintained at a temperature suitable for the formation of poly(propiolactone);
(c) directing the poly(propiolactone) product stream to a second reaction zone, wherein the second reaction zone is maintained at a temperature at or above the pyrolysis temperature of poly(propiolactone) such that the thermal decomposition of poly(propiolactone) produces acrylic acid; and
(d) withdrawing an acrylic acid product stream from the second reaction zone.

In other aspects, provided is a system for converting beta propiolactone to acrylic acid, comprising:
(a) beta propiolactone; and
(b) a cationic solid catalyst comprising a carboxylate salt;
wherein at or above the pyrolysis temperature of poly(propiolactone), beta propiolactone begins polymerizing to poly(propiolactone) in the presence of the cationic solid catalyst, which poly(propiolactone) concurrently thermally decomposes to acrylic acid; and
wherein acrylic acid formed in situ maintains the reaction polymerizing beta propiolactone to poly(propiolactone).

In yet other aspects, provided is a system for converting beta propiolactone to acrylic acid, comprising:
(a) a reaction zone comprising beta propiolactone (BPL) and a cationic solid catalyst comprising a carboxylate salt;
wherein at or above the pyrolysis temperature of poly(propiolactone) (PPL). BPL begins polymerizing to PPL, which PPL concurrently thermally decomposes to acrylic acid; and
(b) a return loop for providing acrylic acid to the reaction zone.

Definitions

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

The terms "halo" and "halogen" as used herein refer to an atom selected from fluorine (fluoro, —F), chlorine (chloro, —Cl), bromine (bromo, —Br), and iodine (iodo, —I).

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. In some variations, the aliphatic group is unbranched or branched. In other variations, the aliphatic group is cyclic. Unless otherwise specified, in some variation, aliphatic groups contain 1-30 carbon atoms. In some embodiments, aliphatic groups contain 1-12 carbon atoms. In some embodiments, aliphatic groups contain 1-8 carbon atoms. In some embodiments, aliphatic groups contain 1-6 carbon atoms. In some embodiments, aliphatic groups contain 1-5 carbon atoms, in some embodiments, aliphatic groups contain 1-4 carbon atoms, in yet other embodiments aliphatic groups contain 1-3 carbon atoms, and in yet other embodiments aliphatic groups contain 1-2 carbon atoms. Suitable aliphatic groups include, for example, linear or branched, alkyl, alkenyl, and alkynyl groups, and hybrids thereof such as (cycloalkyl)alkyl, (cycloalkenyl)alkyl or (cycloalkyl)alkenyl.

The term "heteroaliphatic," as used herein, refers to aliphatic groups wherein one or more carbon atoms are independently replaced by one or more atoms selected from the group consisting of oxygen, sulfur, nitrogen, phosphorus, or boron. In some embodiments, one or two carbon atoms are independently replaced by one or more of oxygen, sulfur, nitrogen, or phosphorus. Heteroaliphatic groups may be substituted or unsubstituted, branched or unbranched, cyclic or acyclic, and include "heterocycle," "hetercyclyl," "heterocycloaliphatic," or "heterocyclic" groups. In some variations, the heteroaliphatic group is branched or unbranched. In other variations, the heteroaliphatic group is cyclic. In yet other variations, the heteroaliphatic group is acyclic.

The term "acrylate" or "acrylates" as used herein refer to any acyl group having a vinyl group adjacent to the acyl carbonyl. The terms encompass mono-, di- and tri-substituted vinyl groups. Acrylates may include, for example, acrylate, methacrylate, ethacrylate, cinnamate (3-phenylacrylate), crotonate, tiglate, and senecioate.

The terms "crude acrylic acid" and "glacial acrylic acid", as used herein, describe acrylic acid of relatively low and high purity, respectively. Crude acrylic acid (also called technical grade acrylic acid) has a typical minimum overall purity level of 94% and can be used to make acrylic esters for paint, adhesive, textile, paper, leather, fiber, and plastic additive applications. Glacial acrylic acid has a typical overall purity level ranging from 98% to 99.99% and can be used to make polyacrylic acid for superabsorbent polymers (SAPs) in disposable diapers, training pants, adult incontinence undergarments and sanitary napkins. Polyacrylic acid is also used in compositions for paper and water treatment, and in detergent co-builder applications. In some variations, acrylic acid has a purity of at least 98%, at least 98.5%, at least 99%, at least 99.1%, at least 99.2%, at least 99.3%, at least 99.4%, at least 99.5%, at least 99.6%, at least 99.7%, at least 99.8%, or at least 99.9%; or between 99% and 99.95%, between 99.5% and 99.95%, between 99.6% and 99.95%, between 99.7% and 99.95%, or between 99.8% and 99.95%.

Impurities in glacial acrylic acid are reduced to an extent possible to facilitate a high-degree of polymerization to acrylic acid polymers (PAA) and avoid adverse effects from side products in end applications. For example, aldehyde impurities in acrylic acid hinder polymerization and may discolor the polymerized acrylic acid. Maleic anhydride impurities form undesirable copolymers which may be detrimental to polymer properties. Carboxylic acids, e.g., saturated carboxylic acids that do not participate in the polymerization, can affect the final odor of PAA or SAP-containing products and/or detract from their use. For example, foul odors may emanate from SAP that contains acetic acid or propionic acid and skin irritation may result from SAP that contains formic acid. The reduction or removal of impurities from petroleum-based acrylic acid is costly, whether to produce petroleum-based crude acrylic acid or petroleum-based glacial acrylic acid. Such costly multistage distillations and/or extraction and/or crystallizations steps are generally employed (e.g., as described in U.S. Pat. Nos. 5,705,688 and 6,541,665).

The term "polymer", as used herein, refers to a molecule comprising multiple repeating units. In some variations, the polymer is a molecule of high relative molecular mass, the structure of which comprises the multiple repetition of units derived, actually or conceptually, from molecules of low relative molecular mass. In some embodiments, a polymer is comprised of only one monomer species (e.g., polyethylene oxide). In some embodiments, the polymer is a copolymer, terpolymer, heteropolymer, block copolymer, or tapered heteropolymer of one or more epoxides. In one variation, the polymer may be a copolymer, terpolymer, heteropolymer, block copolymer, or tapered heteropolymer of two or more monomers.

The term "unsaturated", as used herein, means that a moiety has one or more double or triple bonds.

The terms "cycloaliphatic", "carbocycle", or "carbocyclic", used alone or as part of a larger moiety, refer to a saturated or partially unsaturated cyclic aliphatic monocyclic, bicyclic, or polycyclic ring systems, as described herein, having from 3 to 12 members, wherein the aliphatic ring system is optionally substituted as defined above and described herein. Cycloaliphatic groups include, for example, cyclopropyl, cyclobutyl, cyclopentyl, cyclopentenyl, cyclohexyl, cyclohexenyl, cycloheptyl, cycloheptenyl, cyclooctyl, cyclooctenyl, and cyclooctadienyl. In some embodiments, the cycloalkyl has 3-6 carbons. The terms "cycloaliphatic". "carbocycle" or "carbocyclic" also include aliphatic rings that are fused to one or more aromatic or nonaromatic rings, such as decahydronaphthyl or tetrahydronaphthyl, where the radical or point of attachment is on the aliphatic ring. In some embodiments, a carbocyclic groups is bicyclic. In some embodiments, a carbocyclic group is tricyclic. In some embodiments, a carbocyclic group is polycyclic.

The term "alkyl," as used herein, refers to a saturated hydrocarbon radical. In some variations, the alkyl group is a saturated, straight- or branched-chain hydrocarbon radicals derived from an aliphatic moiety containing between one and six carbon atoms by removal of a single hydrogen atom. Unless otherwise specified, in some variations, alkyl groups contain 1-12 carbon atoms. In some embodiments, alkyl groups contain 1-8 carbon atoms. In some embodiments, alkyl groups contain 1-6 carbon atoms. In some embodiments, alkyl groups contain 1-5 carbon atoms, in some embodiments, alkyl groups contain 1-4 carbon atoms, in yet other embodiments alkyl groups contain 1-3 carbon atoms, and in yet other embodiments alkyl groups contain 1-2 carbon atoms. Alkyl radicals may include, for example, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, and dodecyl.

The term "alkenyl," as used herein, denotes a monovalent group having at least one carbon-carbon double bond. In some variations, the alkenyl group is a monovalent group derived from a straight- or branched-chain aliphatic moiety having at least one carbon-carbon double bond by the removal of a single hydrogen atom. Unless otherwise specified, in some variations, alkenyl groups contain 2-12 carbon atoms. In some embodiments, alkenyl groups contain 2-8 carbon atoms. In some embodiments, alkenyl groups contain 2-6 carbon atoms. In some embodiments, alkenyl groups contain 2-5 carbon atoms, in some embodiments, alkenyl groups contain 2-4 carbon atoms, in yet other embodiments alkenyl groups contain 2-3 carbon atoms, and in yet other embodiments alkenyl groups contain 2 carbon atoms. Alkenyl groups include, for example, ethenyl, propenyl, butenyl, and 1-methyl-2-buten-1-yl.

The term "alkynyl," as used herein, refers to a monovalent group having at least one carbon-carbon triple bond. In some variations, the alkynyl group is a monovalent group derived from a straight- or branched-chain aliphatic moiety having at least one carbon-carbon triple bond by the removal of a single hydrogen atom. Unless otherwise specified, in some variations, alkynyl groups contain 2-12 carbon atoms. In some embodiments, alkynyl groups contain 2-8 carbon atoms. In some embodiments, alkynyl groups contain 2-6 carbon atoms. In some embodiments, alkynyl groups contain 2-5 carbon atoms, in some embodiments, alkynyl groups contain 2-4 carbon atoms, in yet other embodiments alkynyl groups contain 2-3 carbon atoms, and in yet other embodiments alkynyl groups contain 2 carbon atoms. Representative alkynyl groups include, for example, ethynyl, 2-propynyl (propargyl), and 1-propynyl.

The term "carbocycle" and "carbocyclic ring" as used herein, refers to monocyclic and polycyclic moieties wherein the rings contain only carbon atoms. Unless otherwise specified, carbocycles may be saturated, partially unsaturated or aromatic, and contain 3 to 20 carbon atoms. Representative carbocyles include, for example, cyclopropane, cyclobutane, cyclopentane, cyclohexane, bicyclo[2,2,1]heptane, norbornene, phenyl, cyclohexene, naphthalene, and spiro[4.5]decane.

The term "aryl" used alone or as part of a larger moiety as in "aralkyl", "aralkoxy", or "aryloxyalkyl", refers to monocyclic and polycyclic ring systems having a total of five to 20 ring members, wherein at least one ring in the system is aromatic and wherein each ring in the system contains three to twelve ring members. The term "aryl" may be used interchangeably with the term "aryl ring". In some embodiments, "aryl" refers to an aromatic ring system which includes, for example, phenyl, naphthyl, and anthracyl, which may bear one or more substituents. Also included within the scope of the term "aryl", as it is used herein, is a group in which an aromatic ring is fused to one or more additional rings, such as benzofuranyl, indanyl, phthalimidyl, naphthimidyl, phenanthridinyl, and tetrahydronaphthyl.

The terms "heteroaryl" and "heteroar-", used alone or as part of a larger moiety, e.g., "heteroaralkyl", or "heteroaralkoxy", refer to groups having 5 to 14 ring atoms, preferably 5, 6, 9 or 10 ring atoms; having 6, 10, or 14 pi (π) electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, benzofuranyl and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring", "heteroaryl group", or "heteroaromatic", any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle", "heterocyclyl", "heterocyclic radical", and "heterocyclic ring" are used interchangeably and may be saturated or partially unsaturated, and have, in addition to carbon atoms, one or more, preferably one to four, heteroatoms, as defined above. In some variations, the heterocyclic group is a stable 5- to 7-membered monocyclic or 7- to 14-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, for example, tetrahydrofuranyl, tetrahydrothienyl, pyrrolidinyl, pyrrolidonyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle", "heterocyclyl", "heterocyclyl ring", "heterocyclic group", "heterocyclic moiety", and "heterocyclic radical", are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds described herein may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned are preferably those that result in the formation of stable or chemically feasible compounds. The term "stable", as used herein, refers to compounds that are not substantially altered when subjected to conditions to allow for their production, detection, and, in some embodiments, their recovery, purification, and use for one or more of the purposes disclosed herein.

In some chemical structures herein, substituents are shown attached to a bond which crosses a bond in a ring of the depicted molecule. This means that one or more of the substituents may be attached to the ring at any available position (usually in place of a hydrogen atom of the parent structure). In cases where an atom of a ring so substituted has two substitutable positions, two groups may be present on the same ring atom. When more than one substituent is present, each is defined independently of the others, and each may have a different structure. In cases where the substituent shown crossing a bond of the ring is —R, this has the same meaning as if the ring were said to be "optionally substituted" as described in the preceding paragraph.

Suitable monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH—CHPh, which may be substituted with R°; —$NO_2$, —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)N(R°)_2$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR°$, —$SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; $(CH_2)_{0-4}S(O)_2OR°$; —$(CH_2)_{0-4}OS(O)_2R°$; $S(O)_2NR°$, —$(CH_2)S(O)R°$; —$N(R°)S(O)_2NR°_2$; —$N(R°)S(O)_2R°$; —$N(OR°)R°$; —$C(NH)NR°_2$; —$P(O)_2R°$; —$P(O)R°$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-8}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur, or, notwithstanding the definition above, two independent occurrences of R°, taken together with their intervening atom(s), form a 3-12-membered saturated, partially unsaturated, or aryl mono- or polycyclic ring having 0-4 heteroatoms independently selected from nitrogen, oxygen, and sulfur, which may be substituted as defined below.

Suitable monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-4}C(O)N(R^•)_2$; —$(CH_2)_{0-2}SR^•$, —$(CH_2)_{0-2}SH$, —$(CH_2)_{0-2}NH_2$, —$(CH)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —$SSR^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur. Suitable divalent substituents on a saturated carbon atom of R° include =O and =S.

Suitable divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of R is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur. Suitable divalent substituents that are bound to vicinal substitutable carbons of an "optionally substituted" group include: —$O(CR^*_2)_{2-3}O$—, wherein each independent occurrence of R$^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, and sulfur.

Suitable substituents on the aliphatic group of R" include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

Suitable substituents on a substitutable nitrogen of an "optionally substituted" group include —R$^†$, —$NR^†_2$, —C(O)R$^†$, —C(O)OR$^†$, —C(O)C(O)R$^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each R$^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, and sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, and sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, and sulfur.

As used herein, the term "catalyst" refers to a substance the presence of which increases the rate of a chemical reaction, while not being consumed or undergoing a permanent chemical change itself.

As used herein, the term "about" preceding one or more numerical values means the numerical value ±5%. It should be understood that reference to "about" a value or parameter herein includes (and describes) embodiments that are directed to that value or parameter per se. For example, description referring to "about x" includes description of "x" per se.

DETAILED DESCRIPTION

Another route to produce acrylic acid from beta propiolactone (BPL) first polymerizes BPL to poly(propiolactone)

(PPL), which is then isolated and fed into a pyrolysis unit where it thermally decomposes to acrylic acid. The processes and systems described herein provide a direct route for producing acrylic acid from BPL, without isolation of the PPL intermediate. Thus, in one aspect, provided is the direct conversion of BPL to glacial acrylic acid (e.g., GAA) without isolation of PPL. In some embodiments, provided is concurrent polymerization and pyrolysis steps to directly convert BPL to acrylic acid (e.g., GAA) without isolation of PPL. In certain embodiments, conversion of BPL to PPL is performed in the presence of a polymerization catalyst. In some embodiments, polymerization of BPL to PPL occurs first followed by pyrolysis as part of a continuous process. By avoiding the need to isolate, store, and/or transport PPL, the streamlined preparation of acrylic acid (e.g., GAA) from BPL offers cost and manufacturing efficiencies that were not previously obtainable.

In certain embodiments, provided are methods for the conversion of BPL to acrylic acid product streams.

I. Methods

In one aspect, provided are integrated processes and methods for the conversion of BPL to acrylic acid. In certain embodiments, provided are integrated processes for the conversion of BPL to acrylic acid in the presence of a polymerization catalyst without the need to isolate PPL as a separate intermediate product.

In some embodiments, provided is a method for the synthesis of acrylic acid comprising:
(a) providing a feedstock stream comprising beta propiolactone;
(b) directing the feedstock stream to a reaction zone where the feedstock stream is contacted with a polymerization catalyst and where at least a portion of the beta propiolactone is converted to poly(propiolactone);
(c) maintaining the reaction zone at a temperature at or above the pyrolysis temperature of poly(propiolactone) such that the thermal decomposition of poly(propiolactone) produces acrylic acid; and
(d) withdrawing an acrylic acid product stream from the reaction zone;
wherein steps (b) and (c) occur in the same reaction zone.

In some embodiments, provided is a method for the synthesis of acrylic acid comprising:
(a) providing a feedstock stream comprising beta propiolactone;
(b) directing the feedstock stream to a first reaction zone where the feedstock stream is contacted with a polymerization catalyst and where at least a portion of the beta propiolactone is converted to a poly(propiolactone) product stream, wherein the first reaction zone is maintained at a temperature suitable for the formation of poly(propiolactone);
(c) directing the poly(propiolactone) product stream to a second reaction zone, wherein the second reaction zone is maintained at a temperature at or above the pyrolysis temperature of poly(propiolactone) such that the thermal decomposition of poly(propiolactone) produces acrylic acid; and
(d) withdrawing an acrylic acid product stream from the second reaction zone.

It should generally be understood that reference to "a first reaction zone" or "a second reaction zone", etc. does not necessarily imply an order of the reaction zones. In some variations, the use of such references denotes the number of reaction zones present. In other variations, an order may be implied by the context in which the reaction zones are configured, used or present.

In some variations of the foregoing aspects and embodiments, the polymerization catalyst is a carboxylate catalyst.

In some embodiments, provided method for producing acrylic acid, comprising:
(a) providing a feedstock stream comprising beta propiolactone;
(b) directing the feedstock stream to a reaction zone;
(c) contacting the feedstock stream with a polymerization catalyst in the reaction zone;
(d) converting at least a portion of the beta propiolactone to poly(propiolactone) in the reaction zone;
(e) maintaining the reaction zone at a temperature at or above the pyrolysis temperature of poly(propiolactone) such that the thermal decomposition of poly(propiolactone) produces acrylic acid; and
(f) withdrawing an acrylic acid product stream from the reaction zone;
wherein steps (h) and (e) occur in the same reaction zone.

In one embodiment, provided is a method for producing acrylic acid, comprising:
(a) providing a feedstock stream comprising beta propiolactone;
(b) directing the feedstock stream to a reaction zone;
(c) contacting the feedstock stream with a polymerization catalyst in the reaction zone;
(d) polymerizing at least a portion of the beta propiolactone to poly(propiolactone) in the reaction zone, wherein the temperature of the reaction zone is at or above the pyrolysis temperature of poly(propiolactone);
(e) thermally decomposing the poly(propiolactone) in the reaction zone to produce acrylic acid; and
(f) withdrawing an acrylic acid product stream comprising the acrylic acid from the reaction zone;
wherein steps (b) and (e) occur in the same reaction zone.

In the embodiment described above, the production of the poly(propiolactone) and the thermal decomposition of the poly(propiolactone) produced occurs simultaneously in the reaction zone.

The sections below describe more fully certain embodiments of the steps of the methods and conditions utilized to effect each step.

BPL Conversion to PPL

A beta-lactone feedstock stream used in accordance with provided methods and systems may be provided from any one or more of a number of known sources of BPL Methods of making BPL are known in the art and include those described in WO2013/063191 and WO2014/004858. In some embodiments, a feedstock stream comprising BPL enters a reaction zone described herein as a gas or as a liquid. The conversion of BPL to PPL may be performed in either the gas phase or the liquid phase and may be performed neat, or in the presence of a carrier gas, solvent, or other diluent. In some embodiments, a BPL feedstock stream is neat.

It will be appreciated that in certain embodiments, the methods and systems described herein can also be directly integrated to the formation of ethylene oxide, thus avoiding the isolation and storage of this toxic and potentially explosive intermediate. In certain embodiments, the processes described herein are fed by ethylene gas which is converted to ethylene oxide, the ethylene oxide then feeds a second reaction where carbonylation takes place to yield a feedstock stream comprising BPL.

In certain embodiments, conversion of BPL to PPL is performed in a continuous flow format. In certain embodiments, conversion of BPL to PPL is performed in a continuous flow format in the gas phase. In certain embodiments, conversion of BPL to PPL is performed in a continuous flow format in the liquid phase. In certain embodiments, conversion of BPL to PPL is performed in a liquid phase in a batch or semi-batch format. Conversion of BPL to PPL may be performed under a variety of conditions. In certain embodiments, the reaction may be performed in the presence of one or more polymerization catalysts that facilitate the transformation of the BPL to PPL. In one embodiment, the reaction may be performed in the presence of one or more carboxylate catalysts that facilitate the transformation of the BPL to PPL.

In certain embodiments, a feedstock stream comprising BPL is directed to a reaction zone where it is contacted with a polymerization catalyst and where at least a portion of the BPL is converted to PPL. In one embodiment, a feedstock stream comprising BPL is directed to a reaction zone where it is contacted with a carboxylate catalyst and where at least a portion of the BPL is converted to PPL. In some embodiments, the reaction zone is maintained at a temperature suitable for the formation of PPL. In some embodiments, such temperature maintenance comprises the removal of heat from the reaction zone.

In some embodiments, a feedstock stream comprising BPL is directed to a first reaction zone where it is contacted with a polymerization catalyst and where at least a portion of the BPL is converted to a PPL product stream. In one embodiment, a feedstock stream comprising BPL is directed to a first reaction zone where it is contacted with a carboxylate catalyst and where at least a portion of the BPL is converted to a PPL product stream. In some embodiments, the first reaction zone is maintained at a temperature suitable for the formation of PPL. In some embodiments, such temperature maintenance comprises the removal of heat from the first reaction zone.

In certain embodiments, conversion of BPL to PPL utilizes a solid polymerization catalyst and the conversion is conducted at least partially in the gas phase. In certain embodiments, the solid polymerization catalyst in the beta lactone conversion stage comprises a solid acrylic acid catalyst. In certain embodiments, BPL is introduced as a liquid and contacted with a solid polymerization catalyst to form PPL, which undergoes pyrolysis and acrylic acid is removed as a gaseous stream. In other embodiments, BPL is introduced as a gas, contacted with a solid polymerization catalyst to form PPL, which undergoes pyrolysis and acrylic acid is removed as a gaseous stream.

In some variations, conversion of BPL to PPL utilizes a solid carboxylate catalyst and the conversion is conducted at least partially in the gas phase. In certain embodiments, the solid carboxylate catalyst in the beta lactone conversion stage comprises a solid acrylic acid catalyst. In certain embodiments, BPL is introduced as a liquid and contacted with a solid carboxylate catalyst to form PPL which undergoes pyrolysis and acrylic acid is removed as a gaseous stream. In other embodiments, BPL is introduced as a gas, contacted with a solid carboxylate catalyst to form PPL, which undergoes pyrolysis and acrylic acid is removed as a gaseous stream.

In certain embodiments, processes described herein are characterized in that the feed rates, reaction rates, and reactor sizes are scaled such that each subsequent stage in the process can utilize essentially all of the effluent from the previous stage. In certain embodiments, methods include one or more steps of modulating one or more system parameters selected from the group consisting of: the temperature and/or pressure of the lactone conversion stage, the temperature and/or pressure of the pyrolysis stage, and a combination of any two or more of these parameters. In certain embodiments, this modulation of system parameters is performed such that the conversion rate per unit time of each stage matches that of the previous stage so that the effluent of the previous stage may be used directly to feed the subsequent stage. In certain embodiments, methods include one or more steps of analyzing the effluent from one or more stages to assess its content. In certain embodiments, such analyzing steps include performing spectroscopy (e.g., infrared spectroscopy, nuclear magnetic resonance spectroscopy, ultraviolet or visible light spectroscopy and the like), chromatography (e.g., gas or liquid chromatography). In certain embodiments, such analyzing steps include performing physical analyses (e.g., viscosity measurements, refractive index measurement, density measurement of conductivity measurement). In certain embodiments, such analyses are performed in a flow-through or stop-flow mode that provides real-time data on the chemical composition of the effluent. In certain embodiments, such data are used to provide a prompt to adjust one or more of the system parameters described above.

As described above, in some embodiments a two-step process is utilized where at least a portion of BPL is converted to a PPL product stream in a first reaction zone, wherein the first reaction zone is maintained at a temperature suitable for the formation of PPL. In some embodiments, the temperature of a first reaction zone is maintained at or below the pyrolysis temperature of polypropiolactone. In some embodiments, the temperature of a first reaction zone is maintained at or below about 150° C. In some embodiments, the temperature of a first reaction zone is maintained at about 0° C. to about 150° C. In some embodiments, the temperature of a first reaction zone is maintained at about 25° C. to about 150° C. In some embodiments, the temperature of a first reaction zone is maintained at about 50° C. to about 150° C. In some embodiments, the temperature of a first reaction zone is maintained at about 75° C. to about 150° C. In some embodiments, the temperature of a first reaction zone is maintained at about 100° C. to about 150° C. In some embodiments, the temperature of a first reaction zone is maintained at about 0° C. to about 100° C. In some embodiments, the temperature of a first reaction zone is maintained at about 50° C. to about 100° C.

PPL Pyrolysis

As described above, in one aspect, BPL is converted to GAA without isolation of the intermediate PPL. In some embodiments, the PPL formed by polymerization of BPL is concurrently converted to acrylic acid (e.g., GAA) via pyrolysis in the same reaction zone (e.g., a "one-pot" method). In some embodiments, the reaction zone containing the reaction of BPL to PPL is maintained at a temperature at or above the pyrolysis temperature of PPL such that the thermal decomposition of PPL produces acrylic acid. Without wishing to be bound by any particular theory, it is believed that in such embodiments as BPL reacts with acrylic acid to start polymer chains, thermal decomposition will degrade the polymer to acrylic acid.

In certain embodiments, a PPL product stream described above as forming in a first reaction zone is directed to a second reaction zone, wherein the second reaction zone is maintained at a temperature at or above the pyrolysis temperature of PPL such that the thermal decomposition of PPL produces acrylic acid. In some embodiments, the temperature of a first reaction zone is different than the temperature of a second reaction zone. In some embodiments, the temperature of a first reaction zone is below the pyrolysis temperature of PPL. Such embodiments may also be described as a "two-step" method, wherein at least a portion of BPL is converted to PPL prior to entering a reaction zone maintained at or above the pyrolysis temperature. In some embodiments, the PPL product stream entering a second reaction zone comprises an amount of unreacted BPL. In other words, the formation of PPL need not be complete prior to a PPL product stream entering a second reaction zone, and in such cases BPL may undergo polymerization to PPL followed by pyrolysis within the second reaction zone.

A one-pot BPL conversion to acrylic acid can be operated within a variety of temperature and pressure ranges. In some embodiments, the temperature can range from about 150° C. to about 400° C. In some embodiments, the temperature ranges from about 150° C. to about 300° C. In some embodiments, the temperature ranges from about 150° C. to about 250° C. In some embodiments, the temperature ranges from about 175° C. to about 300° C. In some embodiments, the temperature ranges from about 200° C. to about 250° C. In some embodiments, the temperature ranges from about 225° C. to about 275° C. In some embodiments, the temperature ranges from about 250° C. to about 300° C. In some embodiments, the temperature ranges from about 200° C. to about 300° C.

In some embodiments, a two-step process is utilized where pyrolysis proceeds in a second reaction zone and the second reaction zone is maintained at a temperature at or above the pyrolysis temperature of poly(propiolactone). In some embodiments, the temperature of a second reaction zone is maintained at or above about 150° C. In some embodiments, the temperature of a second reaction zone is maintained at or above about 160° C. In some embodiments, the temperature of a second reaction zone is maintained at or above about 175° C. In some embodiments, the temperature of a second reaction zone is maintained at or above about 200° C. In some embodiments, the temperature of a second reaction zone is maintained at or above about 225° C. In some embodiments, the temperature of a second reaction zone is maintained at or above about 250° C. In some embodiments, the temperature of a second reaction zone is maintained at or above about 275° C.

In some embodiments, the pressure used in provided methods and systems can range from about 0.01 atmospheres to about 500 atmospheres (absolute). In some embodiments, the pressure can range from about 0.01 atmospheres to about 10 atmospheres (absolute). In some embodiments, the pressure can range from about 0.01 atmospheres to about 50 atmospheres (absolute). In some embodiments, the pressure can range from about 1 atmosphere to about 10 atmospheres (absolute). In some embodiments, the pressure can range from about 1 atmosphere to about 50 atmospheres (absolute). In some embodiments, the pressure can range from about 1 atmosphere to about 100 atmospheres (absolute). In some embodiments, the pressure can range from about 10 atmospheres to about 50 atmospheres (absolute). In some embodiments, the pressure can range from about 10 atmospheres to about 100 atmospheres (absolute). In some embodiments, the pressure can range from about 50 atmospheres to about 100 atmospheres (absolute). In some embodiments, the pressure can range from about 50 atmospheres to about 200 atmospheres (absolute). In some embodiments, the pressure can range from about 100 atmospheres to about 200 atmospheres (absolute). In some embodiments, the pressure can range from about 100 atmospheres to about 250 atmospheres (absolute). In some embodiments, the pressure can range from about 200 atmospheres to about 300 atmospheres (absolute). In some embodiments, the pressure can range from about 200 atmospheres to about 500 atmospheres (absolute). In some embodiments, the pressure can range from about 250 atmospheres to about 500 atmospheres (absolute).

In some embodiments, the pressure used in provided methods and systems is less than about 5 atmospheres (absolute). In some embodiments, the pressure used in provided methods and systems is less than about 1 atmosphere (absolute). In some embodiments, the pressure can range from about 0.01 atmospheres to about 1 atmosphere (absolute). In some embodiments, the pressure can range from about 0.1 atmospheres to about 0.8 atmospheres (absolute). In some embodiments, the pressure can range from about 0.1 atmospheres to about 0.5 atmospheres (absolute). In some embodiments, the pressure can range from about 0.01 atmospheres to about 0.1 atmospheres (absolute). In some embodiments, the pressure can range from about 0.4 atmospheres to about 1 atmosphere (absolute). In some embodiments, the pressure can range from about 0.05 atmospheres to about 0.1 atmospheres (absolute).

In embodiments where there are two reaction zones, they need not be operated at the same pressure. In certain embodiments the first reaction zone is operated at atmospheric or superatmospheric pressures while the second reaction zone is operated at subatmospheric pressure. In certain embodiments a reaction zone can include a pressure gradient.

Reaction Zones

As used herein, the term "reaction zone" refers to a reactor or portion thereof where a particular reaction occurs. A given reaction may occur in multiple reaction zones, and different reaction zones may comprise separate reactors or portions of the same reactor. A "reactor" typically comprises one or more vessels with one or more connections to other reactors or system components.

In some embodiments of provided methods and systems, a first reaction zone and second reaction zone are comprised within an extruder reactor. In some embodiments, an extruder reactor provides a temperature gradient between a first reaction zone and second reaction zone. It will be appreciated that the temperature of a first reaction zone can be lower than that of a second reaction zone due to the relative temperatures needed to carry out each reaction therein. In some embodiments, an extruder reactor provides a temperature in a first reaction zone of about 0° C. to about 150° C., and a temperature in a second reaction zone of about 150° C. to about 300° C. In some embodiments, the terminal temperature of an extruder is at or above the pyrolysis temperature of PPL. In some variations, terminal temperature refers to the temperature at the exit of the extruder.

Polymerization Catalysts

As described above, polymerizing the BPL to PPL proceeds in the presence of a polymerization catalyst. A variety of catalysts may be used in the polymerization reaction, including by not limited to metals (e.g., lithium, sodium, potassium, magnesium, calcium, zinc, aluminum, titanium, cobalt, etc.) metal oxides, salts of alkali and alkaline earth metals (such as carbonates, borates, hydroxides, alkoxides, and carboxylates), and borates, silicates, or salts of other metals. In certain embodiments, suitable catalysts include carboxylate salts of metal ions. In certain embodiments suitable catalysts include carboxylate salts of organic cations. In some embodiments, a carboxylate salt is other than a carbonate. In some embodiments, a carboxylate salt is acrylate.

In certain embodiments, the polymerization catalyst is combined with BPL in a molar ratio up to about 1:100,000 polymerization catalyst:BPL. In certain embodiments, the ratio is from about 1:100,000 to about 25:100 polymerization catalyst:BPL. In certain embodiments, the polymerization catalyst is combined with BPL in a molar ratio of about 1:50,000 polymerization catalyst:BPL to about 1:25,000 polymerization catalyst:BPL. In certain embodiments, the polymerization catalyst is combined with BPL in a molar ratio of about 1:25,000 polymerization catalyst:BPL to about 1:10,000 polymerization catalyst:BPL. In certain embodiments, the polymerization catalyst is combined with BPL in a molar ratio of about 1:20,000 polymerization catalyst:BPL to about 1:10.000 polymerization catalyst:BPL. In certain embodiments, the polymerization catalyst is combined with BPL in a molar ratio of about 1:15,000 polymerization catalyst:BPL to about 1:5,000 polymerization catalyst:BPL. In certain embodiments, the polymerization catalyst is combined with BPL in a molar ratio of about 1:5,000 polymerization catalyst:BPL to about 1:1,000 polymerization catalyst:BPL. In certain embodiments, the polymerization catalyst is combined with BPL in a molar ratio of about 1:2,000 polymerization catalyst:BPL to about 1:500 polymerization catalyst:BPL In certain embodiments, the polymerization catalyst is combined with BPI, in a molar ratio of about 1:1,000 polymerization catalyst:BPL to about 1:200 polymerization catalyst:BPL In certain embodiments, the polymerization catalyst is combined with BPL in a molar ratio of about 1:500 polymerization catalyst:BPL to about 1:100 polymerization catalyst:BPL In certain embodiments the molar ratio of polymerization catalyst:BPL is about 1:50.000, 1:25,000, 1:15,000, 1:10,000, 1:5,000, 1:1,000, 1:500, 1:250 or a range including any two of these values. In certain embodiments, the polymerization catalyst is combined with BPL in a molar ratio of about 1:100 polymerization catalyst:BPL to about 25:100 polymerization catalyst:BPL. In certain embodiments the molar ratio of polymerization catalyst:BPL is about 1:100, 5:100, 10:100, 15:100, 20:100, 25:100, or a range including any two of these ratios.

In certain embodiments, where the polymerization catalyst comprises a carboxylate salt, the carboxylate has a structure such that upon initiating polymerization of BPL, the polymer chains produced have an acrylate chain end. In certain embodiments, the carboxylate ion on a polymerization catalyst is the anionic form of a chain transfer agent used in the polymerization process.

In certain embodiments, the carboxylate salt of the polymerization catalyst is an acrylate salt (i.e., the anionic form) of a compound of Formula (I):

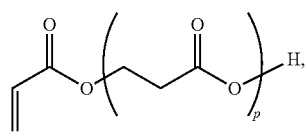

or a mixture of any two or more of these, where p is from 0 to 9. In certain embodiments, p is from 0 to 5. In certain embodiments, the carboxylate salt of the polymerization catalyst is an acrylate salt (i.e., of compound of Formula (I) where p=0).

In certain embodiments, the carboxylate salt of the polymerization catalyst is a salt of an acrylic acid dimer,

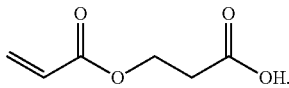

In certain embodiments, the carboxylate salt of the polymerization catalyst is a salt of an acrylic acid trimer,

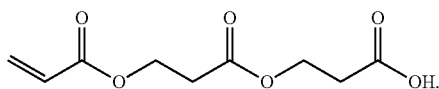

In certain embodiments, where the polymerization catalyst comprises a carboxylate salt, the carboxylate is the anionic form of a $C_{1-40}$ carboxylic acid. In certain embodiments, the carboxylate salt can be a salt of a polycarboxylic acid (e.g. a compound having two or more carboxylic acid groups). In certain embodiments, the carboxylate comprises the anion of a $C_{1-20}$ carboxylic acid. In certain embodiments, the carboxylate comprises the anion of a $C_{1-12}$ carboxylic acid. In certain embodiments, the carboxylate comprises the anion of a $C_{1-8}$ carboxylic acid. In certain embodiments, the carboxylate comprises the anion of a $C_{1-4}$ carboxylic acid. In certain embodiments, the carboxylate comprises the anion of an optionally substituted benzoic acid. In certain embodiments, the carboxylate is selected from the group consisting of: formate, acetate, propionate, valerate, butyrate, $C_{5-10}$ aliphatic carboxylate, and $C_{10-20}$ aliphatic carboxylate.

As noted, in certain embodiments, the polymerization catalyst comprises a carboxylate salt of an organic cation. In certain embodiments, the polymerization catalyst comprises a carboxylate salt of a cation wherein the positive charge is located at least partially on a nitrogen, sulfur, or phosphorus atom. In certain embodiments, the polymerization catalyst comprises a carboxylate salt of a nitrogen cation. In certain embodiments, the polymerization catalyst comprises a carboxylate salt of a cation selected from the group consisting of: ammonium, amidinium, guanidinium, a cationic form of a nitrogen heterocycle, and any combination of two or more of these. In certain embodiments, the polymerization catalyst comprises a carboxylate salt of a phosphorus cation. In certain embodiments, the polymerization catalyst comprises a carboxylate salt of a cation selected from the group consisting of: phosphonium and phosphazenium. In certain embodiments, the polymerization catalyst comprises a carboxylate salt of a sulfur-containing cation. In certain embodiments, the polymerization catalyst comprises a sulfonium salt.

In certain embodiments, the polymerization catalyst comprises a carboxylate salt of a metal. In certain embodiments, the polymerization catalyst comprises a carboxylate salt of a alkali or alkaline earth metal. In certain embodiments, the polymerization catalyst comprises a carboxylate salt of an alkali metal. In certain embodiments, the polymerization catalyst comprises a carboxylate salt of sodium or potassium. In certain embodiments, the polymerization catalyst comprises a carboxylate salt of sodium.

In certain embodiments, the polymerization catalyst comprises a carboxylate salt of a protonated amine:

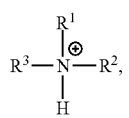

where:
    each R¹ and R² is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein R¹ and R² can be taken together with intervening atoms to form one or more optionally substituted rings optionally containing one or more additional heteroatoms;
    each R³ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur, an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an R³ group can be taken with an R¹ or R² group to form one or more optionally substituted rings.

In certain embodiments where the polymerization catalyst comprises a carboxylate salt of a protonated amine, the protonated amine is selected from the group consisting of:

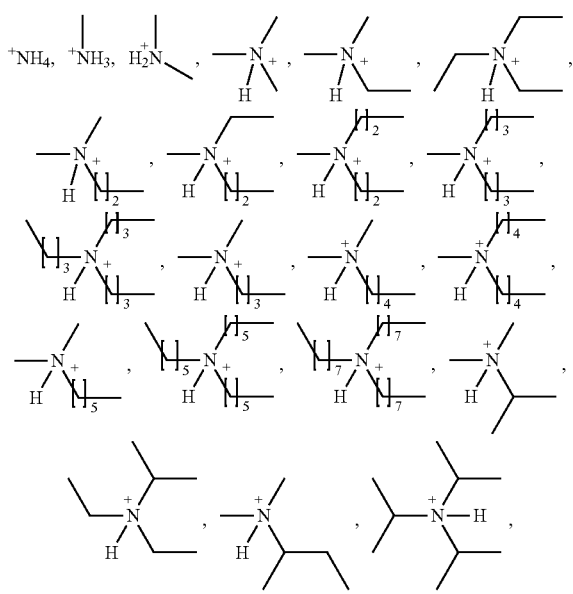

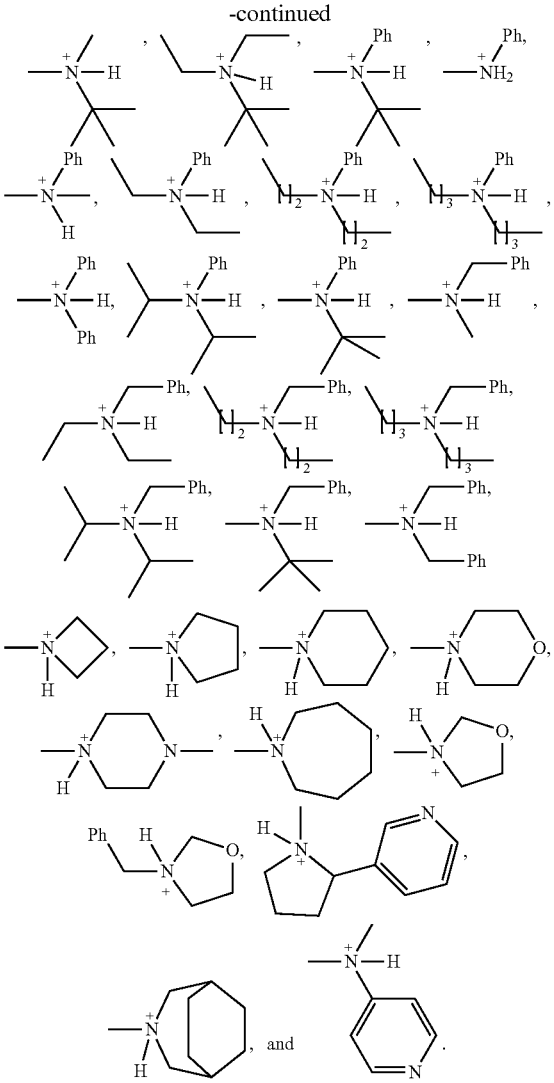

In certain embodiments, the polymerization catalyst comprises a carboxylate salt of a quaternary ammonium salt:

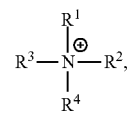

where:
    each R¹, R² and R³ is described above; and
    each R⁴ is independently hydrogen or an optionally substituted radical selected from the group consisting of $C_{1-20}$ aliphatic; $C_{1-20}$ heteroaliphatic; a 3- to 8-membered saturated or partially unsaturated monocyclic carbocycle; a 7- to 14-membered saturated or partially unsaturated polycyclic carbocycle; a 5- to 6-membered monocyclic heteroaryl ring having 1-4 heteroatoms independently selected from nitrogen, oxygen, or sulfur; an 8- to 14-membered polycyclic heteroaryl ring having 1-5 heteroatoms independently selected from nitrogen, oxygen, or sulfur; a 3- to 8-membered saturated or partially unsaturated monocyclic heterocyclic ring having 1-3 heteroatoms independently selected from nitrogen, oxygen, or sulfur; a 6- to 14-membered saturated or partially unsaturated polycyclic heterocycle having 1-5 heteroatoms independently selected from nitrogen, oxygen, or sulfur; phenyl; or an 8- to 14-membered polycyclic aryl ring; wherein an $R^4$ group can be taken with an $R^1$, $R^2$ or $R^3$ group to form one or more optionally substituted rings.

In certain embodiments, a polymerization catalyst comprises a carboxylate salt of a guanidinium group:

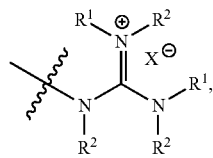

wherein each $R^1$ and $R^2$ is independently as defined above and described in classes and subclasses herein. In certain embodiments, each $R^1$ and $R^2$ is independently hydrogen or $C_{1-2}$ aliphatic. In certain embodiments, each $R^1$ and $R^2$ is independently hydrogen or $C_{1-12}$ aliphatic. In certain embodiments, each $R^1$ and $R^2$ is independently hydrogen or $C_{1-20}$ heteroaliphatic. In certain embodiments, each $R^1$ and $R^2$ is independently hydrogen or phenyl. In certain embodiments, each $R^1$ and $R^2$ is independently hydrogen or 8- to 10-membered aryl. In certain embodiments, each $R^1$ and $R^2$ is independently hydrogen or 5- to 10-membered heteroaryl. In certain embodiments, each $R^1$ and $R^2$ is independently hydrogen or 3- to 7-membered heterocyclic. In certain embodiments, one or more of $R^1$ and $R^2$ is optionally substituted $C_{1-12}$ aliphatic.

In certain embodiments, any two or more $R^1$ or $R^2$ groups are taken together with intervening atoms to form one or more optionally substituted carbocyclic, heterocyclic, aryl, or heteroaryl rings. In certain embodiments, $R^1$ and $R^2$ groups are taken together to form an optionally substituted 5- or 6-membered ring. In certain embodiments, three or more $R^1$ and/or $R^2$ groups are taken together to form an optionally substituted fused ring system.

In certain embodiments, an $R^1$ and $R^2$ group are taken together with intervening atoms to form a compound selected from:

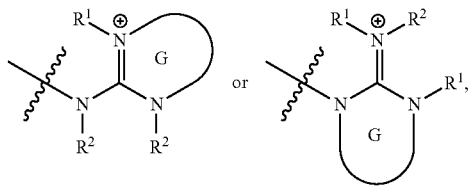

wherein each $R^1$ and $R^2$ is independently as defined above and described in classes and subclasses herein, and Ring G is an optionally substituted 5- to 7-membered saturated or partially unsaturated heterocyclic ring.

It will be appreciated that when a guanidinium cation is depicted as

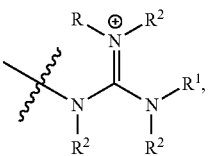

all such resonance forms are contemplated and encompassed by the present disclosure. For example, such groups can also be depicted as

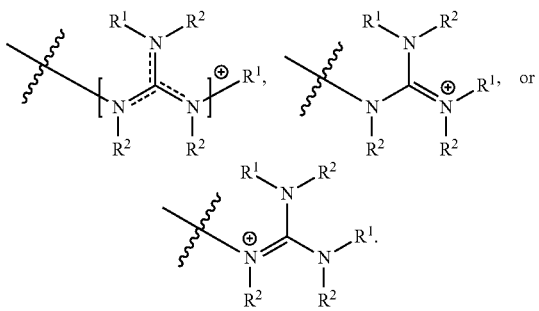

In specific embodiments, a guanidinium cation is selected from the group consisting of:

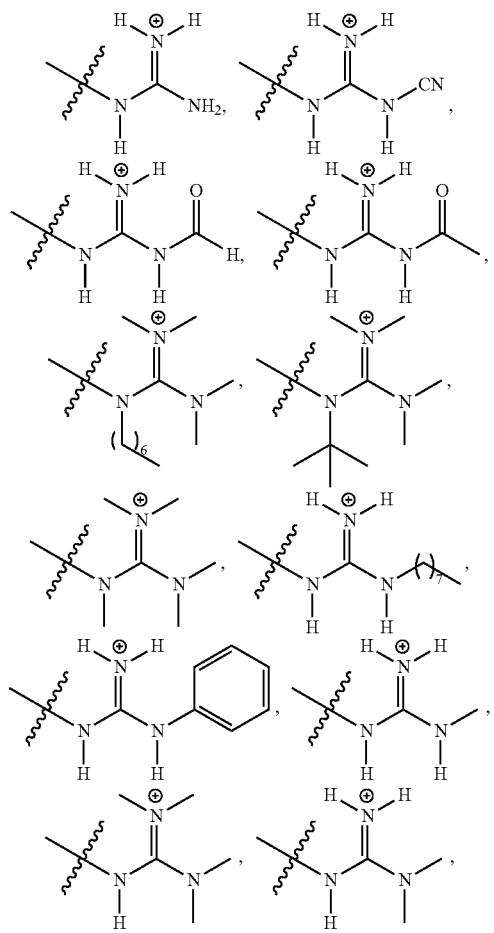

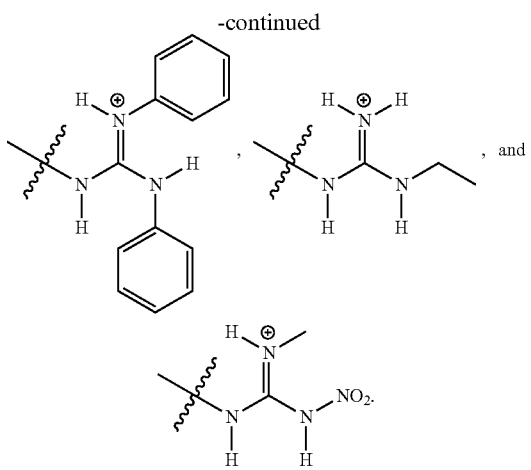

In certain embodiments, a polymerization catalyst comprises a carboxylate salt of a sulfonium group or an arsonium group:

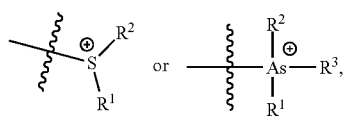

wherein each of $R^1$, $R^2$, and $R^3$ are as defined above and described in classes and subclasses herein.

In specific embodiments, an arsonium cation is selected from the group consisting of:

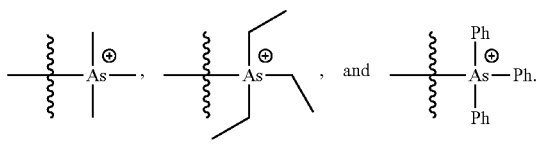

In certain embodiments, a polymerization catalyst comprises a carboxylate salt of an optionally substituted nitrogen-containing heterocycle. In certain embodiments, the nitrogen-containing heterocycle is an aromatic heterocycle. In certain embodiments, the optionally substituted nitrogen-containing heterocycle is selected from the group consisting of: pyridine, imidazole, pyrrolidine, pyrazole, quinoline, thiazole, dithiazole, oxazole, triazole, pyrazolem, isoxazole, isothiazole, tetrazole, pyrazine, thiazine, and triazine.

In certain embodiments, a nitrogen-containing heterocycle includes a quaternarized nitrogen atom. In certain embodiments, a nitrogen-containing heterocycle includes an iminium moiety such as

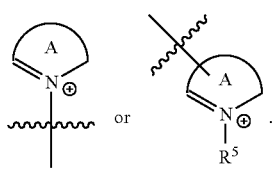

In certain embodiments, the optionally substituted nitrogen-containing heterocycle is selected from the group consisting of pyridinium, imidazolium, pyrrolidinium, pyrazolium, quinolinium, thiazolium, dithiazolium, oxazolium, triazolium, isoxazolium, isothiazolium, tetrazolium, pyrazinium, thiazinium, and triazinium.

In certain embodiments, a nitrogen-containing heterocycle is linked to a metal complex via a ring nitrogen atom. In certain embodiments, a ring nitrogen to which the attachment is made is thereby quaternized, and In certain embodiments, linkage to a metal complex takes the place of an N—H bond and the nitrogen atom thereby remains neutral. In certain embodiments, an optionally substituted N-linked nitrogen-containing heterocycle is a pyridinium derivative. In certain embodiments, optionally substituted N-linked nitrogen-containing heterocycle is an imidazolium derivative. In certain embodiments, optionally substituted N-linked nitrogen-containing heterocycle is a thiazolium derivative. In certain embodiments, optionally substituted N-linked nitrogen-containing heterocycle is a pyridinium derivative.

In certain embodiments, a polymerization catalyst comprises a carboxylate salt of

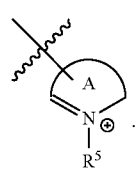

In certain embodiments, ring A is an optionally substituted, 5- to 10-membered heteroaryl group. In certain embodiments, Ring A is an optionally substituted, 6-membered heteroaryl group. In certain embodiments, Ring A is a ring of a fused heterocycle. In certain embodiments, Ring A is an optionally substituted pyridyl group.

In specific embodiments, a nitrogen-containing heterocyclic cation is selected from the group consisting of:

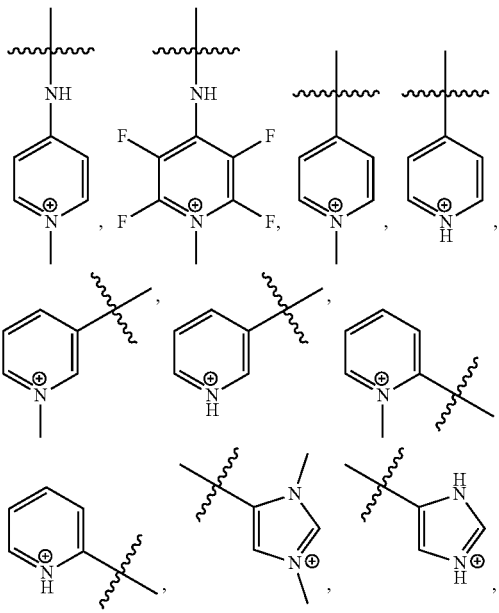

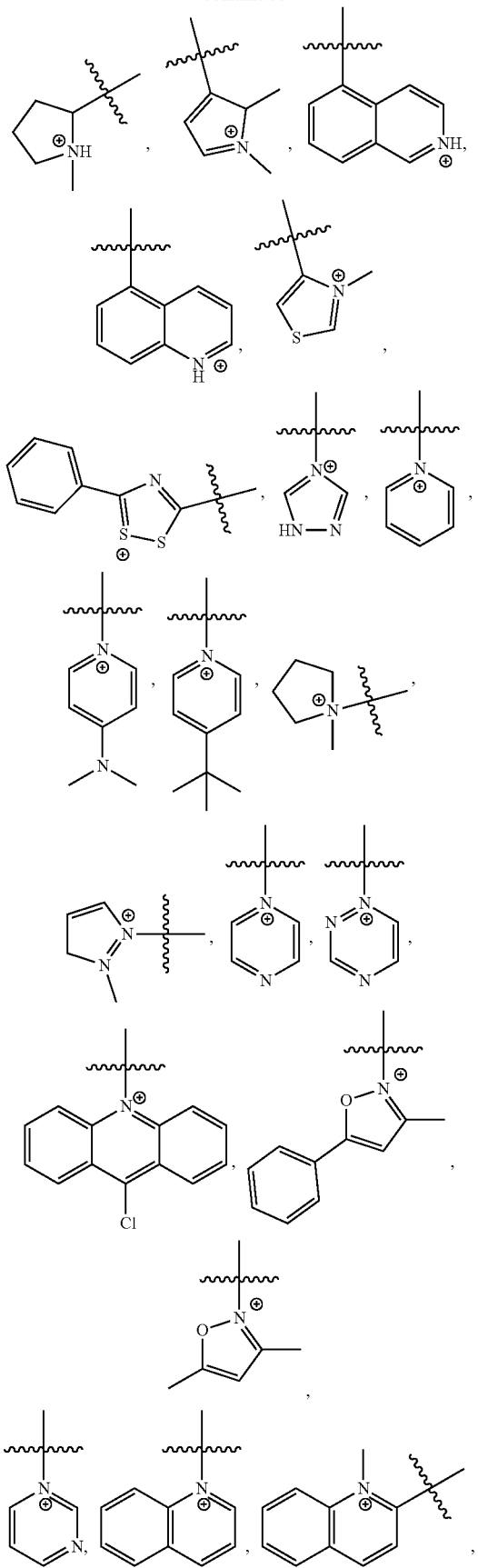

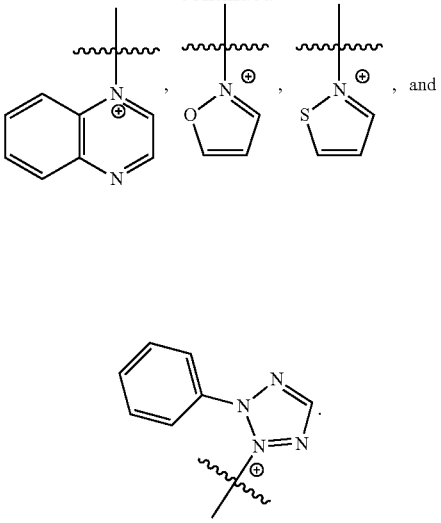

In certain embodiments, a polymerization catalyst comprises a carboxylate salt of

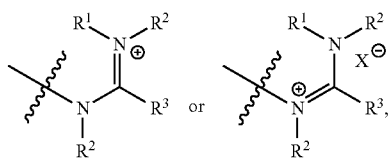

where each $R^1$, $R^2$, and $R^3$ is independently as defined above and described in classes and subclasses herein.

In certain embodiments, a polymerization catalyst comprises a carboxylate salt of

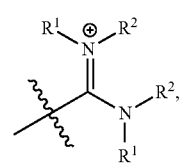

wherein each $R^1$ and $R^2$ is independently as defined above and described in classes and subclasses herein.

In certain embodiments, a polymerization catalyst comprises a carboxylate salt of

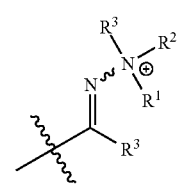

wherein each $R^1$, $R^2$, and $R^3$ is independently as defined above and described in classes and subclasses herein.

In certain embodiments, a polymerization catalyst comprises a carboxylate salt of

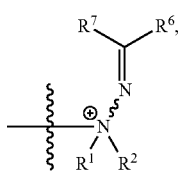

wherein each of $R^1$, $R^2$, $R^6$, and $R^7$ is as defined above and described in classes and subclasses herein.

In certain embodiments, $R^6$ and $R^7$ are each independently an optionally substituted group selected from the group consisting of $C_{1-20}$ aliphatic; $C_{1-20}$ heteroaliphatic; phenyl, and 8-10-membered aryl. In certain embodiments, $R^6$ and $R^7$ are each independently an optionally substituted $C_{1-20}$ aliphatic. In certain embodiments, $R^6$ and $R^7$ are each independently an optionally substituted $C_{1-20}$ heteroaliphatic having. In certain embodiments, $R^6$ and $R^7$ are each independently an optionally substituted phenyl or 8-10-membered aryl. In certain embodiments, $R^6$ and $R^7$ are each independently an optionally substituted 5- to 10-membered heteroaryl. In certain embodiments, $R^6$ and $R^7$ can be taken together with intervening atoms to form one or more rings selected from the group consisting of: optionally substituted $C_3$-$C_{14}$ carbocycle, optionally substituted $C_3$-$C_{14}$ heterocycle, optionally substituted $C_6$-$C_{10}$ aryl, and optionally substituted 5- to 10-membered heteroaryl. In certain embodiments, $R^6$ and $R^7$ are each independently an optionally substituted $C_{1-6}$ aliphatic. In certain embodiments, each occurrence of $R^6$ and $R^7$ is independently methyl, ethyl, propyl, butyl, pentyl, hexyl, heptyl, octyl, or benzyl. In certain embodiments, each occurrence of $R^6$ and $R^7$ is independently perfluoro. In certain embodiments, each occurrence of $R^6$ and $R^7$ is independently —$CF_2CF_3$.

In certain embodiments, a polymerization catalyst comprises a carboxylate salt of

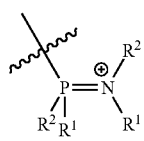

wherein each $R^1$ and $R^2$ is independently as defined above and described in classes and subclasses herein.

In certain embodiments, a polymerization catalyst comprises a carboxylate salt of

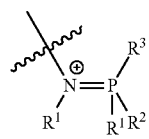

wherein each $R^1$, $R^2$, and $R^3$ is independently as defined above and described in classes and subclasses herein.

In certain embodiments, a cation is

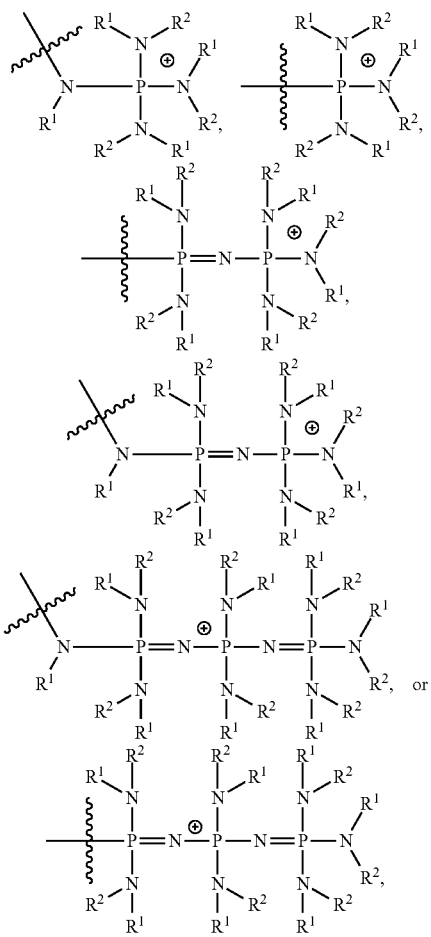

wherein each $R^1$ and $R^2$ is independently as defined above and described in classes and subclasses herein.

In certain embodiments, a polymerization catalyst comprises a carboxylate salt of

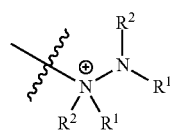

wherein each $R^1$ and $R^2$ is independently as defined above and described in classes and subclasses herein.

In certain embodiments, a polymerization catalyst comprises a carboxylate salt of

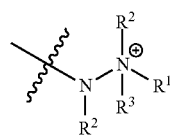

wherein each $R^1$, $R^2$, and $R^3$ is independently as defined above and described in classes and subclasses herein.

In certain embodiments, a polymerization catalyst comprises a carboxylate salt of

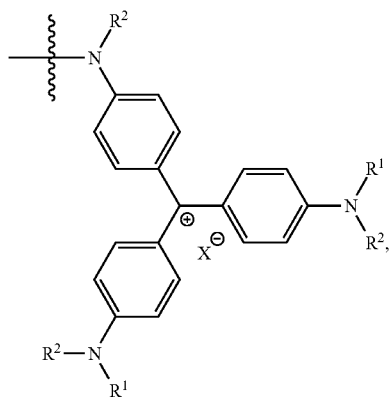

wherein each $R^1$ and $R^2$ is independently as defined above and described in classes and subclasses herein. In certain embodiments, suitable catalysts include transition metal compounds. In certain embodiments, suitable catalysts include acid catalysts. In certain embodiments, the catalyst is a heterogeneous catalyst.

In certain embodiments, any of the foregoing cationic functional groups are attached to a solid support. Examples of suitable solid supports include polymeric solids (e.g. polymer beads, films, fibers, fabric, particles and the like) as well as inorganic solids (e.g. clays, silicas, aluminas, diatomaceous earth, ceramics, metal oxides, mineral fibers beads or particles, and the like). Specific examples of such supported cationic functional groups include polystyrene resin beads functionalized with ammonium groups, polystyrene resin beads functionalized with phosphonium groups, and polystyrene resin beads functionalized with guanidinium groups. Specific examples of such supported cationic functional groups include silica particles functionalized with ammonium groups, alumina particles functionalized with phosphonium groups, and ceramic beads functionalized with guanidinium groups. In certain embodiments, polymerization catalysts comprise carboxylate salts of any of the foregoing supported solid cationic functional groups. In certain embodiments, polymerization catalysts comprise acrylate salts of any of the foregoing supported solid cationic functional groups.

In certain embodiments, polymerization catalysts comprise cationic solids wherein the cations comprise metal atoms. In certain embodiments, polymerization catalysts comprise carboxylate salts of any of the foregoing supported solid cationic metal atoms. In certain embodiments, polymerization catalysts comprise acrylate salts of any of the foregoing supported solid cationic metal atoms.

In certain embodiments, the carboxylate salt of the polymerization catalyst is a compound of Formula (II):

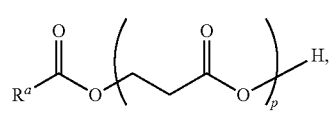

(II)

where p is from 0 to 9 and $R^a$ is a non-volatile moiety. The term "non-volatile moiety," as used herein, refers to a moiety or material to which a carboxylate can be attached, and that renders the carboxylate (e.g., when p=0) non-volatile to pyrolysis conditions. In some embodiments, a non-volatile moiety is selected from the group consisting of glass surfaces, silica surfaces, plastic surfaces, metal surfaces including zeolites, surfaces containing a metallic or chemical coating, membranes (e.g., nylon, polysulfone, silica), microbeads (e.g., latex, polystyrene, or other polymer), and porous polymer matrices (e.g., polyacrylamide, polysaccharide, polymethacrylate). In some embodiments, a non-volatile moiety has a molecular weight above 100, 200, 500, or 1000 g/mol. In some embodiments, a non-volatile moiety is part of a fixed or packed bed system. In some embodiments, a non-volatile moiety is part of a fixed or packed bed system comprising pellets (e.g., zeolite).

In certain embodiments, p is from 0 to 5. In certain embodiments, the carboxylate salt of the polymerization catalyst is an acrylate salt (i.e., of compound of Formula (II) where p=0).

In some embodiments, a suitable polymerization catalyst is heterogeneous. In some embodiments, a suitable polymerization catalyst will remain in a reaction zone as a salt or melt after removal of all other products, intermediates, starting materials, byproducts, and other reaction components. In some embodiments, a suitable polymerization catalyst of Formula (II) will remain in a reaction zone as a salt or melt after removal of all acrylic acid product stream.

In certain embodiments, a catalyst is recycled for further use in a reaction zone. In some embodiments, a salt or melt catalyst is recycled to a reaction zone. In some embodiments, provided methods further comprise withdrawing a recycling stream of homogeneous catalyst from a reaction zone. In some embodiments, such a recycling stream comprises a high boiling solvent, wherein the solvent's boiling point is above the pyrolysis temperature of PPL and the catalyst remains in the high boiling solvent during pyrolysis while the withdrawn product stream is gaseous.

Acrylate Recycling

It will be appreciated by the skilled artisan that the polymerization mode of PPL from BPL proceeds in a manner contrary to the typical polyester polymerization. While polyesters are generally formed by the attack of a hydroxyl group at the carbonyl of a carboxylic group, the strain of the BPL ring affords a unique reactivity wherein a carboxylate anion attacks at the beta carbon, resulting in a terminal carboxylate which may then react with another unit of BPL to propagate the polymer chain:

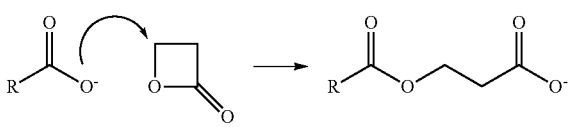

In some embodiments of provided methods, the polymerization of BPL to PPL is catalyzed by an acrylate. Resulting polymer chains will then comprise acrylate end groups. In some embodiments, a carboxylate required to initiate polymerization is acrylic acid provided via a return loop from a product stream. In some embodiments, a portion of acrylic acid produced by a provided method is returned to a reaction zone to initiate polymerization. In some embodiments, acrylic acid formed in situ in a provided method is sufficient to initiate and maintain the conversion of BPL to PPL.

Heat Capturing

In some embodiments of provided methods, heat generated from one portion of a process is captured. For example, polymerization of BPL to PPL is an exothermic process and excess heat generated from the reaction may be captured. In certain embodiments, captured heat is low grade heat. In some embodiments of provided methods, heat generated from a first reaction zone is captured and directed to other processes. In certain embodiments, heat is directed to a second reaction zone. In certain embodiments, heat is directed to an upstream carbonylation process used to provide BPL. In some embodiments, heat is directed to keep a product stream (e.g., acrylic acid vapor) at an appropriate temperature.

Reaction Mode

The methods herein place no particular limits on the type, size or geometry of the reactor employed and indeed, in some cases, more than one reactor may be employed. It is to be understood that the term "reactor" as recited in the methods herein may actually represent more than one physical reactor (for example the reactor could be a train of continuous stirred tank reactors (CSTRs) connected in parallel or in series, or a plurality of plug flow reactors). In some embodiments, the "reactor" referred to in the methods herein may also comprise more than one type of reactor (for example the reactor could comprise a series of extruder reactors). Many such combinations are known in the art and could be employed by the skilled artisan to achieve an efficient reaction in the methods described herein.

Solvents

As used herein, the term "high boiling solvent" refers to a solvent having a boiling point higher than that of the pyrolysis temperature of PPL. In some embodiments, a high boiling point solvent has a boiling point higher than 150° C. In some embodiments, a high boiling point solvent has a boiling point higher than 180° C. In some embodiments, a high boiling point solvent has a boiling point higher than 200° C. In some embodiments, a high boiling point solvent has a boiling point higher than 220° C. Boiling points used herein are the boiling points at a pressure of 1 atm.

II. Systems

In another aspect, provided are systems for the synthesis of acrylic acid. In some embodiments, a system for the conversion of beta propiolactone to acrylic acid comprises:
(a) beta propiolactone (BPL); and
(b) a cationic solid catalyst comprising a carboxylate salt,
wherein at or above the pyrolysis temperature of poly (propiolactone) (PPL), BPL begins polymerizing to PPL in the presence of the cationic solid catalyst, which PPL concurrently thermally decomposes to acrylic acid;
wherein acrylic acid formed in situ maintains the reaction polymerizing BPL to PPL.

In some variations, provided is a system for converting beta propiolactone to acrylic acid, comprising:
a beta propiolactone (BPL) source;
a catalyst source; and
a reactor comprising:
at least one inlet to receive BPL from the BPL source and a polymerization catalyst from the catalyst source, wherein the polymerization catalyst comprises a carboxylate salt, and
an outlet to output an acrylic acid stream,
wherein the reactor is configured to (i) polymerize the BPL to produce poly(propiolactone) (PPL) in the presence of the polymerization catalyst, at or above the pyrolysis temperature of PPL, and (ii) concurrently thermally decompose the PPL to produce acrylic acid in situ, and wherein the acrylic acid produced in situ maintains the polymerization of BPL to PPL.

In some embodiments, the polymerization catalyst is a cationic solid catalyst comprising a carboxylate salt.

As mentioned above, in some embodiments provided methods comprise a return loop of acrylic acid product to a reactor. Thus, in some embodiments, a system for the conversion of beta propiolactone to acrylic acid comprises:
(a) a reaction zone comprising beta propiolactone (BPL) and a polymerization catalyst comprising a carboxylate salt;
wherein at or above the pyrolysis temperature of poly (propiolactone) (PPL), BPL begins polymerizing to PPL, which PPL concurrently thermally decomposes to acrylic acid; and
(b) a return loop for providing acrylic acid to the reaction zone.

In some variations, provided is a system for converting beta propiolactone to acrylic acid, comprising:
a reaction zone comprising beta propiolactone (BPL) and a cationic solid catalyst comprising a carboxylate salt, wherein the reaction zone is configured to (i) polymerize BPL to poly(propiolactone) (PPL) in the presence of the cationic solid catalyst, at or above the pyrolysis temperature of PPL, and (ii) concurrently thermally decomposes the PPL to acrylic acid; and
a return loop for providing acrylic acid to the reaction zone.

It should be understood that any of the cationic solid catalysts described herein may be used in the systems of the foregoing embodiments and variations.

ENUMERATED EMBODIMENTS

The following enumerated embodiments are representative of some aspects of the invention.

1. A method for the synthesis of acrylic acid comprising the steps of:
(a) providing a feedstock stream comprising beta propiolactone;
(b) directing the feedstock stream to a reaction zone where it is contacted with a suitable carboxylate catalyst and where at least a portion of the beta propiolactone is converted to poly(propiolactone);
(c) maintaining the reaction zone at a temperature at or above the pyrolysis temperature of poly(propiolactone) such that the thermal decomposition of poly(propiolactone) produces acrylic acid; and
(d) withdrawing an acrylic acid product stream from the reaction zone;
wherein steps (b) and (c) occur in the same reaction zone.

2. The method of embodiment 1, further comprising directing a return loop of a portion of the acrylic acid product stream to the reaction zone.

3. A method for the synthesis of acrylic acid comprising the steps of:
(a) providing a feedstock stream comprising beta propiolactone;
(b) directing the feedstock stream to a first reaction zone where it is contacted with a suitable carboxylate catalyst and where at least a portion of the beta propiolactone is converted to a poly(propiolactone) product stream, wherein the first reaction zone is maintained at a temperature suitable for the formation of poly(propiolactone);

(c) directing the poly(propiolactone) product stream to a second reaction zone, wherein the second reaction zone is maintained at a temperature at or above the pyrolysis temperature of poly(propiolactone) such that the thermal decomposition of poly(propiolactone) produces acrylic acid; and
(d) withdrawing an acrylic acid product stream from the second reaction zone.

4. The method of embodiment 2, wherein the first reaction zone and second reaction zone are comprised within an extruder reactor.
5. The method of embodiment 4, wherein the extruder reactor provides a temperature gradient between the first reaction zone and second reaction zone.
6. The method of embodiment 5, wherein the terminal temperature of the extruder is at or above the pyrolysis temperature of poly(propiolactone).
7. The method of any one of embodiments 3-6, further comprising the step of capturing heat generated from the first reaction zone and directing the heat to other processes.
8. The method of embodiment 7, wherein the heat is directed to the second reaction zone.
9. The method of any one of the preceding embodiments, wherein the suitable carboxylate catalyst is a salt of a compound of formula:

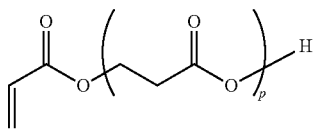

wherein p is 0 to 9.
10. The method of any one of embodiments 1-8, wherein the suitable carboxylate catalyst is a salt of a compound of formula:

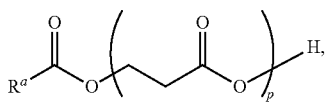

where p is from 0 to 9 and $R^a$ is a non-volatile moiety.
11. The method of any one of the preceding embodiments, wherein the suitable carboxylate catalyst is heterogeneous.
12. The method of any one of the preceding embodiments, wherein after removal of all acrylic acid product stream, the suitable carboxylate catalyst remains in the reaction zone as a salt or melt.
13. The method of embodiment 12, wherein the salt or melt is then recycled to the reaction zone.
14. The method of any one of the preceding embodiments, wherein the feedstock stream contains or is combined with a high boiling solvent.
15. The method of embodiment 14, further comprising the step of withdrawing a recycling stream of the suitable carboxylate catalyst to the reaction zone.
16. The method of any one of the preceding embodiments, further comprising directing a return loop of a portion of the acrylic acid product stream to the reaction zone.
17. The method of any one of the preceding embodiments, wherein the beta propiolactone feedstock stream is neat.
18. A system for the conversion of beta propiolactone to acrylic acid comprising:

(a) beta propiolactone; and
(b) a cationic solid catalyst comprising a carboxylate salt;
wherein at or above the pyrolysis temperature of poly(propiolactone), beta propiolactone begins polymerizing to poly(propiolactone) in the presence of the cationic solid catalyst, which poly(propiolactone) concurrently thermally decomposes to acrylic acid; and
wherein acrylic acid formed in situ maintains the reaction polymerizing beta propiolactone to poly(propiolactone).

19. A system for the conversion of beta propiolactone to acrylic acid comprising:
(a) a reaction zone comprising beta propiolactone (BPL) and a cationic solid catalyst comprising a carboxylate salt;
wherein at or above the pyrolysis temperature of poly(propiolactone) (PPL), BPL begins polymerizing to PPL, which PPL concurrently thermally decomposes to acrylic acid; and
(b) a return loop for providing acrylic acid to the reaction zone.

20. A method for producing acrylic acid, comprising:
(a) providing a feedstock stream comprising beta propiolactone;
(b) directing the feedstock stream to a reaction zone;
(c) contacting the feedstock stream with a polymerization catalyst in the reaction zone;
(d) polymerizing at least a portion of the beta propiolactone to poly(propiolactone) in the reaction zone, wherein the temperature of the reaction zone is at or above the pyrolysis temperature of poly(propiolactone);
(e) thermally decomposing the poly(propiolactone) in the reaction zone to produce acrylic acid; and
(f) withdrawing an acrylic acid product stream comprising the acrylic acid from the reaction zone;
wherein steps (b) and (e) occur in the same reaction zone.

21. The method of embodiment 20, further comprising directing a return loop comprising a portion of the acrylic acid product stream to the reaction zone.
22. The method of embodiment 21, wherein the return loop of acrylic acid is combined with the feedstock stream.
23. A method for producing acrylic acid, comprising:
(a) providing a feedstock stream comprising beta propiolactone;
(b) directing the feedstock stream to a first reaction zone;
(c) contacting the feedstock stream with a polymerization catalyst;
(d) polymerizing at least a portion of the beta propiolactone to a poly(propiolactone) product stream, wherein the first reaction zone is maintained at a temperature to promote formation of poly(propiolactone);
(e) directing the poly(propiolactone) product stream to a second reaction zone, wherein the second reaction zone is maintained at a temperature at or above the pyrolysis temperature of poly(propiolactone) such that the thermal decomposition of poly(propiolactone) produces acrylic acid; and
(f) withdrawing an acrylic acid product stream from the second reaction zone.

24. The method of embodiment 23, wherein the first reaction zone and second reaction zone are in an extruder reactor.
25. The method of embodiment 24, wherein the extruder reactor provides a temperature gradient between the first reaction zone and second reaction zone.

26. The method of embodiment 24 or 25, wherein the extruder reactor has a terminal temperature at or above the pyrolysis temperature of poly(propiolactone).
27. The method of any one of embodiments 23 to 26, further comprising capturing heat generated from the first reaction zone, and directing the heat to other processes.
28. The method of embodiment 27, wherein the heat is directed to the second reaction zone.
29. The method of any one of embodiments 20 to 28, wherein the polymerization catalyst is a salt of a compound of formula:

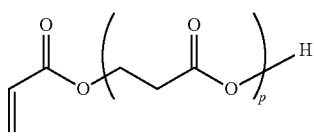

wherein p is 0 to 9.
30. The method of any one of embodiments 20 to 28, wherein the polymerization catalyst is a salt of a compound of formula:

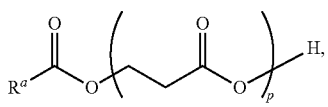

where p is from 0 to 9 and $R^a$ is a non-volatile moiety.
31. The method of any one of embodiments 20 to 30, wherein the polymerization catalyst is heterogeneous.
32. The method of any one of embodiments 20 to 31, wherein after removal of all acrylic acid product stream, the polymerization catalyst remains as a salt or melt.
33. The method of embodiment 32, further comprising recycling the salt or melt to the reaction zone.
34. The method of any one of embodiments 20 to 33, wherein the feedstock stream contains or is combined with a high boiling solvent.
35. The method of embodiment 34, further comprising withdrawing a recycling stream of the polymerization catalyst from the reaction zone.
36. The method of any one of embodiments 20 to 35, further comprising directing a return loop of a portion of the acrylic acid product stream to the reaction zone.
37. The method of any one of embodiments 20 to 36, wherein the feedstock stream is neat.
38. A system for converting beta propiolactone to acrylic acid, comprising:
   (a) beta propiolactone; and
   (b) a cationic solid catalyst comprising a carboxylate salt, wherein at or above the pyrolysis temperature of poly(propiolactone), beta propiolactone begins polymerizing to poly(propiolactone) in the presence of the cationic solid catalyst, which poly(propiolactone) concurrently thermally decomposes to acrylic acid, and wherein acrylic acid formed in situ maintains the reaction polymerizing beta propiolactone to poly(propiolactone).
39. A system for converting beta propiolactone to acrylic acid, comprising:
   (a) a reaction zone comprising beta propiolactone (BPL) and a cationic solid catalyst comprising a carboxylate salt,
   wherein at or above the pyrolysis temperature of poly(propiolactone) (PPL), BPL begins polymerizing to PPL, which PPL concurrently thermally decomposes to acrylic acid; and
   (b) a return loop for providing acrylic acid to the reaction zone.
40. The system of embodiment 38 or 39, wherein the carboxylate salt is:
   a salt of a compound of formula:

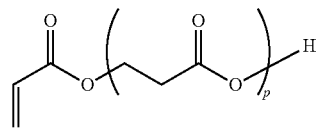

wherein p is 0 to 9; or
   a salt of a compound of formula:

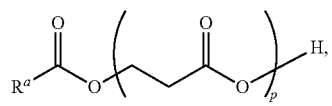

where p is from 0 to 9 and $R^a$ is a non-volatile moiety.

What is claimed is:

1. A system for converting beta propiolactone to acrylic acid, comprising:
   (a) a beta propiolactone source;
   (b) a catalyst source; and
   (c) a reactor comprising:
      at least one inlet to receive beta propiolactone from the beta propiolactone source and a polymerization catalyst from the catalyst source, wherein the polymerization catalyst comprises a carboxylate salt, and
      an outlet to output an acrylic acid stream,
   wherein the reactor is configured to (i) polymerize the beta propiolactone to produce poly(propiolactone) in the presence of the polymerization catalyst, at or above the pyrolysis temperature of poly(propiolactone), and (ii) concurrently thermally decompose the poly(propiolactone) to produce acrylic acid in situ, and wherein the acrylic acid produced in situ maintains the polymerization of beta propiolactone to poly(propiolactone).

2. The system of claim 1, wherein the carboxylate salt is:
   a salt of a compound of formula:

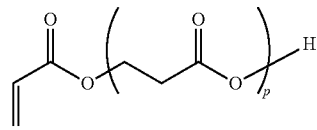

wherein p is 0 to 9.

3. The system of claim 1, wherein the carboxylate salt is: a salt of a compound of formula:

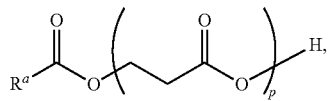

where p is from 0 to 9 and $R^a$ is a non-volatile moiety.

4. A system for converting beta propiolactone to acrylic acid, comprising:
   (a) a reaction zone comprising beta propiolactone and a cationic solid catalyst comprising a carboxylate salt, wherein the reaction zone is configured to (i) polymerize the beta propiolactone to poly(propiolactone), at or above the pyrolysis temperature of poly(propiolactone), (ii) concurrently thermally decompose the poly(propiolactone) to acrylic acid, and (iii) output the acrylic acid; and
   (b) a return loop configured to return a portion of the acrylic acid to the reaction zone to maintain polymerization of the beta propiolactone to poly(propiolactone) in the reaction zone.

5. The system of claim 4, wherein the carboxylate salt is: a salt of a compound of formula:

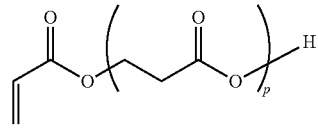

wherein p is 0 to 9.

6. The system of claim 4, wherein the carboxylate salt is: a salt of a compound of formula:

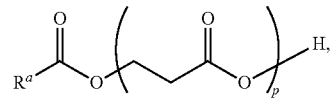

where p is from 0 to 9 and $R^a$ is a non-volatile moiety.

* * * * *